(12) United States Patent
Triman et al.

(10) Patent No.: US 11,389,093 B2
(45) Date of Patent: Jul. 19, 2022

(54) LOW NOISE OXIMETRY CABLE

(71) Applicant: MASIMO CORPORATION, Irvine, CA (US)

(72) Inventors: Benjamin C. Triman, Rancho Santa Margarita, CA (US); John Schmidt, Lake Forest, CA (US)

(73) Assignee: MASIMO CORPORATION, Irvine, CA (US)

( * ) Notice: Subject to any disclaimer, the term of this patent is extended or adjusted under 35 U.S.C. 154(b) by 286 days.

(21) Appl. No.: 16/598,385

(22) Filed: Oct. 10, 2019

(65) Prior Publication Data

US 2020/0113497 A1  Apr. 16, 2020

Related U.S. Application Data

(60) Provisional application No. 62/744,308, filed on Oct. 11, 2018.

(51) Int. Cl.
 A61B 5/1455 (2006.01)
 H01B 7/04 (2006.01)
 H01B 7/18 (2006.01)

(52) U.S. Cl.
 CPC .......... *A61B 5/14551* (2013.01); *H01B 7/04* (2013.01); *H01B 7/1805* (2013.01); *H01B 7/1875* (2013.01); *A61B 2562/12* (2013.01); *A61B 2562/222* (2013.01)

(58) Field of Classification Search
 CPC . A61B 5/0059; A61B 5/0205; A61B 5/02427; A61B 5/1455; A61B 5/14551; A61B 5/14552; A61B 2562/222
 See application file for complete search history.

(56) References Cited

U.S. PATENT DOCUMENTS

| 3,644,659 | A | * | 2/1972 | Campbell | H01B 11/10 174/27 |
| 4,461,923 | A | * | 7/1984 | Bogese, II | H01B 11/1091 174/106 SC |
| 4,960,128 | A | | 10/1990 | Gordon et al. | |
| 4,964,408 | A | | 10/1990 | Hink et al. | |
| 5,041,187 | A | | 8/1991 | Hink et al. | |
| 5,069,213 | A | | 12/1991 | Polczynski | |
| 5,149,915 | A | * | 9/1992 | Brunker | H01B 11/02 174/105 R |
| 5,163,438 | A | | 11/1992 | Gordon et al. | |
| 5,319,355 | A | | 6/1994 | Russek | |
| 5,337,744 | A | | 8/1994 | Branigan | |
| 5,341,805 | A | | 8/1994 | Stavridi et al. | |
| D353,195 | S | | 12/1994 | Savage et al. | |

(Continued)

*Primary Examiner* — Chu Chuan Liu
(74) *Attorney, Agent, or Firm* — Knobbe, Martens, Olson & Bear, LLP

(57) ABSTRACT

The present disclosure includes a cable for a patient monitoring system. The cable can have a flexible and durable overall construction that enables the cable to withstand repeated winding and unwinding and prevent kinks from developing. The cable may include multiple bundles encased in inner jackets that reduce the amount of friction against other cable elements and allows the bundle to move more freely inside an outer jacket of the cable. The multiple bundles may include multiple wires or cords. The cable can include a flexible core that runs through the middle of the cable. The multiple bundles can be twisted, weaved, or untwisted around the core.

25 Claims, 4 Drawing Sheets

(56) References Cited

U.S. PATENT DOCUMENTS

| | | |
|---|---|---|
| D353,196 S | 12/1994 | Savage et al. |
| 5,377,676 A | 1/1995 | Vari et al. |
| D359,546 S | 6/1995 | Savage et al. |
| 5,431,170 A | 7/1995 | Mathews |
| 5,436,499 A | 7/1995 | Namavar et al. |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,490,505 A | 2/1996 | Diab et al. |
| 5,494,043 A | 2/1996 | O'Sullivan et al. |
| 5,533,511 A | 7/1996 | Kaspari et al. |
| 5,534,851 A | 7/1996 | Russek |
| 5,561,275 A | 10/1996 | Savage et al. |
| 5,562,002 A | 10/1996 | Lalin |
| 5,590,649 A | 1/1997 | Caro et al. |
| 5,602,924 A | 2/1997 | Durand et al. |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,645,440 A | 7/1997 | Tobler et al. |
| 5,671,914 A | 9/1997 | Kalkhoran et al. |
| 5,685,299 A | 11/1997 | Diab et al. |
| 5,726,440 A | 3/1998 | Kalkhoran et al. |
| D393,830 S | 4/1998 | Tobler et al. |
| 5,743,262 A | 4/1998 | Lepper, Jr. et al. |
| 5,747,806 A | 5/1998 | Khalil et al. |
| 5,750,994 A | 5/1998 | Schlager |
| 5,758,644 A | 6/1998 | Diab et al. |
| 5,760,910 A | 6/1998 | Lepper, Jr. et al. |
| 5,769,785 A | 6/1998 | Diab et al. |
| 5,782,757 A | 7/1998 | Diab et al. |
| 5,785,659 A | 7/1998 | Caro et al. |
| 5,791,347 A | 8/1998 | Flaherty et al. |
| 5,810,734 A | 9/1998 | Caro et al. |
| 5,823,950 A | 10/1998 | Diab et al. |
| 5,830,131 A | 11/1998 | Caro et al. |
| 5,833,618 A | 11/1998 | Caro et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,919,134 A | 7/1999 | Diab |
| 5,934,925 A | 8/1999 | Tobler et al. |
| 5,940,182 A | 8/1999 | Lepper, Jr. et al. |
| 5,987,343 A | 11/1999 | Kinast |
| 5,995,855 A | 11/1999 | Kiani et al. |
| 5,997,343 A | 12/1999 | Mills et al. |
| 6,002,952 A | 12/1999 | Diab et al. |
| 6,010,937 A | 1/2000 | Karam et al. |
| 6,011,986 A | 1/2000 | Diab et al. |
| 6,027,452 A | 2/2000 | Flaherty et al. |
| 6,036,642 A | 3/2000 | Diab et al. |
| 6,040,578 A | 3/2000 | Malin et al. |
| 6,045,509 A | 4/2000 | Caro et al. |
| 6,066,204 A | 5/2000 | Haven |
| 6,067,462 A | 5/2000 | Diab et al. |
| 6,081,735 A | 6/2000 | Diab et al. |
| 6,088,607 A | 7/2000 | Diab et al. |
| 6,110,522 A | 8/2000 | Lepper, Jr. et al. |
| 6,115,673 A | 9/2000 | Malin et al. |
| 6,124,597 A | 9/2000 | Shehada |
| 6,128,521 A | 10/2000 | Marro et al. |
| 6,129,675 A | 10/2000 | Jay |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,184,521 B1 | 2/2001 | Coffin, IV et al. |
| 6,206,830 B1 | 3/2001 | Diab et al. |
| 6,229,856 B1 | 5/2001 | Diab et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,255,708 B1 | 7/2001 | Sudharsanan et al. |
| 6,256,523 B1 | 7/2001 | Diab et al. |
| 6,263,222 B1 | 7/2001 | Diab et al. |
| 6,278,522 B1 | 8/2001 | Lepper, Jr. et al. |
| 6,280,213 B1 | 8/2001 | Tobler et al. |
| 6,280,381 B1 | 8/2001 | Malin et al. |
| 6,285,896 B1 | 9/2001 | Tobler et al. |
| 6,301,493 B1 | 10/2001 | Marro et al. |
| 6,308,089 B1 | 10/2001 | von der Ruhr et al. |
| 6,317,627 B1 | 11/2001 | Ennen et al. |
| 6,321,100 B1 | 11/2001 | Parker |
| 6,325,761 B1 | 12/2001 | Jay |
| 6,334,065 B1 | 12/2001 | Al-Ali et al. |
| 6,343,224 B1 | 1/2002 | Parker |
| 6,349,228 B1 | 2/2002 | Kiani et al. |
| 6,360,114 B1 | 3/2002 | Diab et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,388,240 B2 | 5/2002 | Schulz et al. |
| 6,397,091 B2 | 5/2002 | Diab et al. |
| 6,411,373 B1 | 6/2002 | Garside et al. |
| 6,415,167 B1 | 7/2002 | Blank et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,487,429 B2 | 11/2002 | Hockersmith et al. |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,525,386 B1 | 2/2003 | Mills et al. |
| 6,526,300 B1 | 2/2003 | Kiani et al. |
| 6,534,012 B1 | 3/2003 | Hazen et al. |
| 6,541,756 B2 | 4/2003 | Schulz et al. |
| 6,542,764 B1 | 4/2003 | Al-Ali et al. |
| 6,580,086 B1 | 6/2003 | Schulz et al. |
| 6,584,336 B1 | 6/2003 | Ali et al. |
| 6,587,196 B1 | 7/2003 | Stippick et al. |
| 6,587,199 B1 | 7/2003 | Luu |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,632,181 B2 | 10/2003 | Flaherty et al. |
| 6,635,559 B2 | 10/2003 | Greenwald et al. |
| 6,639,668 B1 | 10/2003 | Trepagnier |
| 6,640,116 B2 | 10/2003 | Diab |
| 6,640,117 B2 | 10/2003 | Makarewicz et al. |
| 6,643,530 B2 | 11/2003 | Diab et al. |
| 6,650,917 B2 | 11/2003 | Diab et al. |
| 6,654,624 B2 | 11/2003 | Diab et al. |
| 6,658,276 B2 | 12/2003 | Kiani et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,738,652 B2 | 5/2004 | Mattu et al. |
| 6,745,060 B2 | 6/2004 | Diab et al. |
| 6,760,607 B2 | 7/2004 | Al-Ali |
| 6,770,028 B1 | 8/2004 | Ali et al. |
| 6,771,994 B2 | 8/2004 | Kiani et al. |

(56) References Cited

U.S. PATENT DOCUMENTS

| | | |
|---|---|---|
| 6,788,965 B2 | 9/2004 | Ruchti et al. |
| 6,792,300 B1 | 9/2004 | Diab et al. |
| 6,813,511 B2 | 11/2004 | Diab et al. |
| 6,816,241 B2 | 11/2004 | Grubisic |
| 6,816,741 B2 | 11/2004 | Diab |
| 6,822,564 B2 | 11/2004 | Al-Ali |
| 6,826,419 B2 | 11/2004 | Diab et al. |
| 6,830,711 B2 | 12/2004 | Mills et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,861,639 B2 | 3/2005 | Al-Ali |
| 6,876,931 B2 | 4/2005 | Lorenz et al. |
| 6,898,452 B2 | 5/2005 | Al-Ali et al. |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |
| 6,956,649 B2 | 10/2005 | Acosta et al. |
| 6,961,598 B2 | 11/2005 | Diab |
| 6,970,792 B1 | 11/2005 | Diab |
| 6,979,812 B2 | 12/2005 | Al-Ali |
| 6,985,764 B2 | 1/2006 | Mason et al. |
| 6,990,364 B2 | 1/2006 | Ruchti et al. |
| 6,993,371 B2 | 1/2006 | Kiani et al. |
| 6,996,427 B2 | 2/2006 | Ali et al. |
| 6,998,247 B2 | 2/2006 | Monfre et al. |
| 6,999,904 B2 | 2/2006 | Weber et al. |
| 7,003,338 B2 | 2/2006 | Weber et al. |
| 7,003,339 B2 | 2/2006 | Diab et al. |
| 7,015,451 B2 | 3/2006 | Dalke et al. |
| 7,024,233 B2 | 4/2006 | Ali et al. |
| 7,027,849 B2 | 4/2006 | Al-Ali |
| 7,030,749 B2 | 4/2006 | Al-Ali |
| 7,039,449 B2 | 5/2006 | Al-Ali |
| 7,041,060 B2 | 5/2006 | Flaherty et al. |
| 7,044,918 B2 | 5/2006 | Diab |
| 7,048,687 B1 | 5/2006 | Reuss et al. |
| 7,067,893 B2 | 6/2006 | Mills et al. |
| D526,719 S | 8/2006 | Richie, Jr. et al. |
| 7,096,052 B2 | 8/2006 | Mason et al. |
| 7,096,054 B2 | 8/2006 | Abdul-Hafiz et al. |
| D529,616 S | 10/2006 | Deros et al. |
| 7,132,641 B2 | 11/2006 | Schulz et al. |
| 7,133,710 B2 | 11/2006 | Acosta et al. |
| 7,135,641 B2 * | 11/2006 | Clark ............... H01B 7/184 174/110 R |
| 7,142,901 B2 | 11/2006 | Kiani et al. |
| 7,149,561 B2 | 12/2006 | Diab |
| 7,186,966 B2 | 3/2007 | Al-Ali |
| 7,190,261 B2 | 3/2007 | Al-Ali |
| 7,215,984 B2 | 5/2007 | Diab |
| 7,215,986 B2 | 5/2007 | Diab |
| 7,221,971 B2 | 5/2007 | Diab |
| 7,225,006 B2 | 5/2007 | Al-Ali et al. |
| 7,225,007 B2 | 5/2007 | Al-Ali |
| RE39,672 E | 6/2007 | Shehada et al. |
| 7,239,905 B2 | 7/2007 | Kiani-Azarbayjany et al. |
| 7,245,953 B1 | 7/2007 | Parker |
| 7,254,429 B2 | 8/2007 | Schurman et al. |
| 7,254,431 B2 | 8/2007 | Al-Ali |
| 7,254,433 B2 | 8/2007 | Diab et al. |
| 7,254,434 B2 | 8/2007 | Schulz et al. |
| 7,272,425 B2 | 9/2007 | Al-Ali |
| 7,274,955 B2 | 9/2007 | Kiani et al. |
| D554,263 S | 10/2007 | Al-Ali |
| 7,280,858 B2 | 10/2007 | Al-Ali et al. |
| 7,289,835 B2 | 10/2007 | Mansfield et al. |
| 7,292,883 B2 | 11/2007 | De Felice et al. |
| 7,295,866 B2 | 11/2007 | Al-Ali |
| 7,328,053 B1 | 2/2008 | Diab et al. |
| 7,332,784 B2 | 2/2008 | Mills et al. |
| 7,340,287 B2 | 3/2008 | Mason et al. |
| 7,341,559 B2 | 3/2008 | Schulz et al. |
| 7,343,186 B2 | 3/2008 | Lamego et al. |
| D566,282 S | 4/2008 | Al-Ali et al. |
| 7,355,512 B1 | 4/2008 | Al-Ali |
| 7,356,365 B2 | 4/2008 | Schurman |
| 7,371,981 B2 | 5/2008 | Abdul-Hafiz |
| 7,373,193 B2 | 5/2008 | Al-Ali et al. |
| 7,373,194 B2 | 5/2008 | Weber et al. |
| 7,376,453 B1 | 5/2008 | Diab et al. |
| 7,377,794 B2 | 5/2008 | Al Ali et al. |
| 7,377,899 B2 | 5/2008 | Weber et al. |
| 7,383,070 B2 | 6/2008 | Diab et al. |
| 7,395,158 B2 | 7/2008 | Monfre et al. |
| 7,415,297 B2 | 8/2008 | Al-Ali et al. |
| 7,428,432 B2 | 9/2008 | Ali et al. |
| 7,438,683 B2 | 10/2008 | Al-Ali et al. |
| 7,440,787 B2 | 10/2008 | Diab |
| 7,454,240 B2 | 11/2008 | Diab et al. |
| 7,467,002 B2 | 12/2008 | Weber et al. |
| 7,469,157 B2 | 12/2008 | Diab et al. |
| 7,471,969 B2 | 12/2008 | Diab et al. |
| 7,471,971 B2 | 12/2008 | Diab et al. |
| 7,483,729 B2 | 1/2009 | Al-Ali et al. |
| 7,483,730 B2 | 1/2009 | Diab et al. |
| 7,489,958 B2 | 2/2009 | Diab et al. |
| 7,496,391 B2 | 2/2009 | Diab et al. |
| 7,496,393 B2 | 2/2009 | Diab et al. |
| D587,657 S | 3/2009 | Al-Ali et al. |
| 7,499,741 B2 | 3/2009 | Diab et al. |
| 7,499,835 B2 | 3/2009 | Weber et al. |
| 7,500,950 B2 | 3/2009 | Al-Ali et al. |
| 7,509,154 B2 | 3/2009 | Diab et al. |
| 7,509,494 B2 | 3/2009 | Al-Ali |
| 7,510,849 B2 | 3/2009 | Schurman et al. |
| 7,514,725 B2 | 4/2009 | Wojtczuk et al. |
| 7,519,406 B2 | 4/2009 | Blank et al. |
| 7,526,328 B2 | 4/2009 | Diab et al. |
| D592,507 S | 5/2009 | Wachman et al. |
| 7,530,942 B1 | 5/2009 | Diab |
| 7,530,949 B2 | 5/2009 | Al Ali et al. |
| 7,530,955 B2 | 5/2009 | Diab et al. |
| 7,563,110 B2 | 7/2009 | Al-Ali et al. |
| 7,593,230 B2 | 9/2009 | Abul-Haj et al. |
| 7,596,398 B2 | 9/2009 | Al-Ali et al. |
| 7,606,608 B2 | 10/2009 | Blank et al. |
| 7,618,375 B2 | 11/2009 | Flaherty |
| 7,620,674 B2 | 11/2009 | Ruchti et al. |
| D606,659 S | 12/2009 | Kiani et al. |
| 7,629,039 B2 | 12/2009 | Eckerbom et al. |
| 7,640,140 B2 | 12/2009 | Ruchti et al. |
| 7,647,083 B2 | 1/2010 | Al-Ali et al. |
| D609,193 S | 2/2010 | Al-Ali et al. |
| D614,305 S | 4/2010 | Al-Ali et al. |
| 7,697,966 B2 | 4/2010 | Monfre et al. |
| 7,698,105 B2 | 4/2010 | Ruchti et al. |
| RE41,317 E | 5/2010 | Parker |
| RE41,333 E | 5/2010 | Blank et al. |
| 7,729,733 B2 | 6/2010 | Al-Ali et al. |
| 7,734,320 B2 | 6/2010 | Al-Ali |
| 7,761,127 B2 | 7/2010 | Al-Ali et al. |
| 7,761,128 B2 | 7/2010 | Al-Ali et al. |
| 7,764,982 B2 | 7/2010 | Dalke et al. |
| D621,516 S | 8/2010 | Kiani et al. |
| 7,791,155 B2 | 9/2010 | Diab |
| 7,801,581 B2 | 9/2010 | Diab |
| 7,822,452 B2 | 10/2010 | Schurman et al. |
| RE41,912 E | 11/2010 | Parker |
| 7,844,313 B2 | 11/2010 | Kiani et al. |
| 7,844,314 B2 | 11/2010 | Al-Ali |
| 7,844,315 B2 | 11/2010 | Al-Ali |
| 7,865,222 B2 | 1/2011 | Weber et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |

(56) References Cited

U.S. PATENT DOCUMENTS

| | | |
|---|---|---|
| 7,909,772 B2 | 3/2011 | Popov et al. |
| 7,910,875 B2 | 3/2011 | Al-Ali |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,976,472 B2 | 7/2011 | Kiani |
| 7,988,637 B2 | 8/2011 | Diab |
| 7,990,382 B2 | 8/2011 | Kiani |
| 7,991,446 B2 | 8/2011 | Al-Ali et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,028,701 B2 | 10/2011 | Al-Ali et al. |
| 8,029,765 B2 | 10/2011 | Bellott et al. |
| 8,036,727 B2 | 10/2011 | Schurman et al. |
| 8,036,728 B2 | 10/2011 | Diab et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| 8,175,672 B2 | 5/2012 | Parker |
| 8,180,420 B2 | 5/2012 | Diab et al. |
| 8,182,443 B1 | 5/2012 | Kiani |
| 8,185,180 B2 | 5/2012 | Diab et al. |
| 8,190,223 B2 | 5/2012 | Al-Ali et al. |
| 8,190,227 B2 | 5/2012 | Diab et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,532 B2 | 7/2012 | Davis |
| 8,229,533 B2 | 7/2012 | Diab et al. |
| 8,233,955 B2 | 7/2012 | Al-Ali et al. |
| 8,244,325 B2 | 8/2012 | Al-Ali et al. |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,280,473 B2 | 10/2012 | Al-Ali |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,315,683 B2 | 11/2012 | Al-Ali et al. |
| RE43,860 E | 12/2012 | Parker |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,364,223 B2 | 1/2013 | Al-Ali et al. |
| 8,364,226 B2 | 1/2013 | Diab et al. |
| 8,374,665 B2 | 2/2013 | Lamego |
| 8,385,995 B2 | 2/2013 | Al-ali et al. |
| 8,385,996 B2 | 2/2013 | Smith et al. |
| 8,388,353 B2 | 3/2013 | Kiani et al. |
| 8,399,822 B2 | 3/2013 | Al-Ali |
| 8,401,602 B2 | 3/2013 | Kiani |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,825 B2 | 5/2013 | Dalvi et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,577,431 B2 | 11/2013 | Lamego et al. |
| 8,581,732 B2 | 11/2013 | Al-Ali et al. |
| 8,584,345 B2 | 11/2013 | Al-Ali et al. |
| 8,588,880 B2 | 11/2013 | Abdul-Hafiz et al. |
| 8,600,467 B2 | 12/2013 | Al-Ali et al. |
| 8,606,342 B2 | 12/2013 | Diab |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,688,183 B2 | 4/2014 | Bruinsma et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,726,496 B2 * | 5/2014 | Besko ............... A61B 5/14552 600/344 |
| 8,740,792 B1 | 6/2014 | Kiani et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |

(56) References Cited

U.S. PATENT DOCUMENTS

| | | |
|---|---|---|
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali et al. |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,886,271 B2 | 11/2014 | Kiani et al. |
| 8,888,539 B2 | 11/2014 | Al-Ali et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,909,310 B2 | 12/2014 | Lamego et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,965,471 B2 | 2/2015 | Lamego |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |
| 9,028,429 B2 | 5/2015 | Telfort et al. |
| 9,037,207 B2 | 5/2015 | Al-Ali et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,713 B2 | 10/2015 | Al-Ali et al. |
| 9,167,995 B2 | 10/2015 | Lamego et al. |
| 9,176,141 B2 | 11/2015 | Al-Ali et al. |
| 9,186,102 B2 | 11/2015 | Bruinsma et al. |
| 9,192,312 B2 | 11/2015 | Al-Ali |
| 9,192,329 B2 | 11/2015 | Al-Ali |
| 9,192,351 B1 | 11/2015 | Telfort et al. |
| 9,195,385 B2 | 11/2015 | Al-Ali et al. |
| 9,211,072 B2 | 12/2015 | Kiani |
| 9,211,095 B1 | 12/2015 | Al-Ali |
| 9,218,454 B2 | 12/2015 | Kiani et al. |
| 9,226,696 B2 | 1/2016 | Kiani |
| 9,241,662 B2 | 1/2016 | Al-Ali et al. |
| 9,245,668 B1 | 1/2016 | Vo et al. |
| 9,259,185 B2 | 2/2016 | Abdul-Hafiz et al. |
| 9,267,572 B2 | 2/2016 | Barker et al. |
| 9,277,880 B2 | 3/2016 | Poeze et al. |
| 9,289,167 B2 | 3/2016 | Diab et al. |
| 9,295,421 B2 | 3/2016 | Kiani et al. |
| 9,307,928 B1 | 4/2016 | Al-Ali et al. |
| 9,323,894 B2 | 4/2016 | Kiani |
| D755,392 S | 5/2016 | Hwang et al. |
| 9,326,712 B1 | 5/2016 | Kiani |
| 9,333,316 B2 | 5/2016 | Kiani |
| 9,339,220 B2 | 5/2016 | Lamego et al. |
| 9,341,565 B2 | 5/2016 | Lamego et al. |
| 9,351,673 B2 | 5/2016 | Diab et al. |
| 9,351,675 B2 | 5/2016 | Al-Ali et al. |
| 9,364,181 B2 | 6/2016 | Kiani et al. |
| 9,368,671 B2 | 6/2016 | Wojtczuk et al. |
| 9,370,325 B2 | 6/2016 | Al-Ali et al. |
| 9,370,326 B2 | 6/2016 | McHale et al. |
| 9,370,335 B2 | 6/2016 | Al-ali et al. |
| 9,375,185 B2 | 6/2016 | Ali et al. |
| 9,386,953 B2 | 7/2016 | Al-Ali |
| 9,386,961 B2 | 7/2016 | Al-Ali et al. |
| 9,392,945 B2 | 7/2016 | Al-Ali et al. |
| 9,397,448 B2 | 7/2016 | Al-Ali et al. |
| 9,408,542 B1 | 8/2016 | Kinast et al. |
| 9,436,645 B2 | 9/2016 | Al-Ali et al. |
| 9,445,759 B1 | 9/2016 | Lamego et al. |
| 9,466,919 B2 | 10/2016 | Kiani et al. |
| 9,474,474 B2 | 10/2016 | Lamego et al. |
| 9,480,422 B2 | 11/2016 | Al-Ali |
| 9,480,435 B2 | 11/2016 | Olsen |
| 9,492,110 B2 | 11/2016 | Al-Ali et al. |
| 9,510,779 B2 | 12/2016 | Poeze et al. |
| 9,517,024 B2 | 12/2016 | Kiani et al. |
| 9,532,722 B2 | 1/2017 | Lamego et al. |
| 9,538,949 B2 | 1/2017 | Al-Ali et al. |
| 9,538,980 B2 | 1/2017 | Telfort et al. |
| 9,549,696 B2 | 1/2017 | Lamego et al. |
| 9,554,737 B2 | 1/2017 | Schurman et al. |
| 9,560,996 B2 | 2/2017 | Kiani |
| 9,560,998 B2 | 2/2017 | Al-Ali et al. |
| 9,566,019 B2 | 2/2017 | Al-Ali et al. |
| 9,579,039 B2 | 2/2017 | Jansen et al. |
| 9,591,975 B2 | 3/2017 | Dalvi et al. |
| 9,622,692 B2 | 4/2017 | Lamego et al. |
| 9,622,693 B2 | 4/2017 | Diab |
| D788,312 S | 5/2017 | Al-Ali et al. |
| 9,636,055 B2 | 5/2017 | Al-Ali et al. |
| 9,636,056 B2 | 5/2017 | Al-Ali |
| 9,649,054 B2 | 5/2017 | Lamego et al. |
| 9,662,052 B2 | 5/2017 | Al-Ali et al. |
| 9,668,679 B2 | 6/2017 | Schurman et al. |
| 9,668,680 B2 | 6/2017 | Bruinsma et al. |
| 9,668,703 B2 | 6/2017 | Al-Ali |
| 9,675,286 B2 | 6/2017 | Diab |
| 9,687,160 B2 | 6/2017 | Kiani |
| 9,693,719 B2 | 7/2017 | Al-Ali et al. |
| 9,693,737 B2 | 7/2017 | Al-Ali |
| 9,697,928 B2 | 7/2017 | Al-Ali et al. |
| 9,717,425 B2 | 8/2017 | Kiani et al. |
| 9,717,458 B2 | 8/2017 | Lamego et al. |
| 9,724,016 B1 | 8/2017 | Al-Ali et al. |
| 9,724,024 B2 | 8/2017 | Al-Ali |
| 9,724,025 B1 | 8/2017 | Kiani et al. |
| 9,730,640 B2 | 8/2017 | Diab et al. |
| 9,743,887 B2 | 8/2017 | Al-Ali et al. |
| 9,749,232 B2 | 8/2017 | Sampath et al. |
| 9,750,442 B2 | 9/2017 | Olsen |
| 9,750,443 B2 | 9/2017 | Smith et al. |
| 9,750,461 B1 | 9/2017 | Telfort |
| 9,775,545 B2 | 10/2017 | Al-Ali et al. |
| 9,775,546 B2 | 10/2017 | Diab et al. |

(56) References Cited

U.S. PATENT DOCUMENTS

| | | |
|---|---|---|
| 9,775,570 B2 | 10/2017 | Al-Ali |
| 9,778,079 B1 | 10/2017 | Al-Ali et al. |
| 9,782,077 B2 | 10/2017 | Lamego et al. |
| 9,782,110 B2 | 10/2017 | Kiani |
| 9,787,568 B2 | 10/2017 | Lamego et al. |
| 9,788,735 B2 | 10/2017 | Al-Ali |
| 9,788,768 B2 | 10/2017 | Al-Ali et al. |
| 9,795,300 B2 | 10/2017 | Al-Ali |
| 9,795,310 B2 | 10/2017 | Al-Ali |
| 9,795,358 B2 | 10/2017 | Telfort et al. |
| 9,795,739 B2 | 10/2017 | Al-Ali et al. |
| 9,801,556 B2 | 10/2017 | Kiani |
| 9,801,588 B2 | 10/2017 | Weber et al. |
| 9,808,188 B1 | 11/2017 | Perea et al. |
| 9,814,418 B2 | 11/2017 | Weber et al. |
| 9,820,691 B2 | 11/2017 | Kiani |
| 9,833,152 B2 | 12/2017 | Kiani et al. |
| 9,833,180 B2 | 12/2017 | Shakespeare et al. |
| 9,839,379 B2 | 12/2017 | Al-Ali et al. |
| 9,839,381 B1 | 12/2017 | Weber et al. |
| 9,847,002 B2 | 12/2017 | Kiani et al. |
| 9,847,749 B2 | 12/2017 | Kiani et al. |
| 9,848,800 B1 | 12/2017 | Lee et al. |
| 9,848,806 B2 | 12/2017 | Al-Ali et al. |
| 9,848,807 B2 | 12/2017 | Lamego |
| 9,861,298 B2 | 1/2018 | Eckerbom et al. |
| 9,861,304 B2 | 1/2018 | Al-Ali et al. |
| 9,861,305 B1 | 1/2018 | Weber et al. |
| 9,867,578 B2 | 1/2018 | Al-Ali et al. |
| 9,872,623 B2 | 1/2018 | Al-Ali |
| 9,876,320 B2 | 1/2018 | Coverston et al. |
| 9,877,650 B2 | 1/2018 | Muhsin et al. |
| 9,877,686 B2 | 1/2018 | Al-Ali et al. |
| 9,891,079 B2 | 2/2018 | Dalvi |
| 9,895,107 B2 | 2/2018 | Al-Ali et al. |
| 9,913,617 B2 | 3/2018 | Al-Ali et al. |
| 9,924,893 B2 | 3/2018 | Schurman et al. |
| 9,924,897 B1 | 3/2018 | Abdul-Hafiz |
| 9,936,917 B2 | 4/2018 | Poeze et al. |
| 9,943,269 B2 | 4/2018 | Muhsin et al. |
| 9,949,676 B2 | 4/2018 | Al-Ali |
| 9,955,937 B2 | 5/2018 | Telfort |
| 9,965,946 B2 | 5/2018 | Al-Ali |
| 9,980,667 B2 | 5/2018 | Kiani et al. |
| D820,865 S | 6/2018 | Muhsin et al. |
| 9,986,919 B2 | 6/2018 | Lamego et al. |
| 9,986,952 B2 | 6/2018 | Dalvi et al. |
| 9,989,560 B2 | 6/2018 | Poeze et al. |
| 9,993,207 B2 | 6/2018 | Al-Ali et al. |
| 10,007,758 B2 | 6/2018 | Al-Ali et al. |
| D822,215 S | 7/2018 | Al-Ali et al. |
| D822,216 S | 7/2018 | Barker et al. |
| 10,010,276 B2 | 7/2018 | Al-Ali et al. |
| 10,032,002 B2 | 7/2018 | Kiani et al. |
| 10,039,482 B2 | 8/2018 | Al-Ali et al. |
| 10,052,037 B2 | 8/2018 | Kinast et al. |
| 10,058,275 B2 | 8/2018 | Al-Ali et al. |
| 10,064,562 B2 | 9/2018 | Al-Ali |
| 10,086,138 B1 | 10/2018 | Novak, Jr. |
| 10,092,200 B2 | 10/2018 | Al-Ali et al. |
| 10,092,249 B2 | 10/2018 | Kiani et al. |
| 10,098,550 B2 | 10/2018 | Al-Ali et al. |
| 10,098,591 B2 | 10/2018 | Al-Ali et al. |
| 10,098,610 B2 | 10/2018 | Al-Ali et al. |
| 10,111,591 B2 | 10/2018 | Dyell et al. |
| D833,624 S | 11/2018 | DeJong et al. |
| 10,123,726 B2 | 11/2018 | Al-Ali et al. |
| 10,123,729 B2 | 11/2018 | Dyell et al. |
| 10,130,289 B2 | 11/2018 | Al-Ali et al. |
| 10,130,291 B2 | 11/2018 | Schurman et al. |
| D835,282 S | 12/2018 | Barker et al. |
| D835,283 S | 12/2018 | Barker et al. |
| D835,284 S | 12/2018 | Barker et al. |
| D835,285 S | 12/2018 | Barker et al. |
| 10,149,616 B2 | 12/2018 | Al-Ali et al. |
| 10,154,815 B2 | 12/2018 | Al-Ali et al. |
| 10,159,412 B2 | 12/2018 | Lamego et al. |
| 10,188,296 B2 | 1/2019 | Al-Ali et al. |
| 10,188,331 B1 | 1/2019 | Al-Ali et al. |
| 10,188,348 B2 | 1/2019 | Kiani et al. |
| RE47,218 E | 2/2019 | Ali-Ali |
| RE47,244 E | 2/2019 | Kiani et al. |
| RE47,249 E | 2/2019 | Kiani et al. |
| 10,194,847 B2 | 2/2019 | Al-Ali |
| 10,194,848 B1 | 2/2019 | Kiani et al. |
| 10,201,298 B2 | 2/2019 | Al-Ali et al. |
| 10,205,272 B2 | 2/2019 | Kiani et al. |
| 10,205,291 B2 | 2/2019 | Scruggs et al. |
| 10,213,108 B2 | 2/2019 | Al-Ali |
| 10,219,706 B2 | 3/2019 | Al-Ali |
| 10,219,746 B2 | 3/2019 | McHale et al. |
| 10,226,187 B2 | 3/2019 | Al-Ali et al. |
| 10,226,576 B2 | 3/2019 | Kiani |
| 10,231,657 B2 | 3/2019 | Al-Ali et al. |
| 10,231,670 B2 | 3/2019 | Blank et al. |
| 10,231,676 B2 | 3/2019 | Al-Ali et al. |
| RE47,353 E | 4/2019 | Kiani et al. |
| 10,251,585 B2 | 4/2019 | Al-Ali et al. |
| 10,251,586 B2 | 4/2019 | Lamego |
| 10,255,994 B2 | 4/2019 | Sampath et al. |
| 10,258,265 B1 | 4/2019 | Poeze et al. |
| 10,258,266 B1 | 4/2019 | Poeze et al. |
| 10,271,748 B2 | 4/2019 | Al-Ali |
| 10,278,626 B2 | 5/2019 | Schurman et al. |
| 10,278,648 B2 | 5/2019 | Al-Ali et al. |
| 10,279,247 B2 | 5/2019 | Kiani |
| 10,292,628 B1 | 5/2019 | Poeze et al. |
| 10,292,657 B2 | 5/2019 | Abdul-Hafiz et al. |
| 10,292,664 B2 | 5/2019 | Al-Ali |
| 10,299,708 B1 | 5/2019 | Poeze et al. |
| 10,299,709 B2 | 5/2019 | Perea et al. |
| 10,299,720 B2 | 5/2019 | Brown et al. |
| 10,305,775 B2 | 5/2019 | Lamego et al. |
| 10,307,111 B2 | 6/2019 | Muhsin et al. |
| 10,325,681 B2 | 6/2019 | Sampath et al. |
| 10,327,337 B2 | 6/2019 | Triman et al. |
| 10,327,713 B2 | 6/2019 | Barker et al. |
| 10,332,630 B2 | 6/2019 | Al-Ali |
| 10,335,033 B2 | 7/2019 | Al-Ali |
| 10,335,068 B2 | 7/2019 | Poeze et al. |
| 10,335,072 B2 | 7/2019 | Al-Ali et al. |
| 10,342,470 B2 | 7/2019 | Al-Ali et al. |
| 10,342,487 B2 | 7/2019 | Al-Ali et al. |
| 10,342,497 B2 | 7/2019 | Al-Ali et al. |
| 10,349,895 B2 | 7/2019 | Telfort et al. |
| 10,349,898 B2 | 7/2019 | Al-Ali et al. |
| 10,354,504 B2 | 7/2019 | Kiani et al. |
| 10,357,206 B2 | 7/2019 | Weber et al. |
| 10,357,209 B2 | 7/2019 | Al-Ali |
| 10,366,787 B2 | 7/2019 | Sampath et al. |
| 10,368,787 B2 | 8/2019 | Reichgott et al. |
| 10,376,190 B1 | 8/2019 | Poeze et al. |
| 10,376,191 B1 | 8/2019 | Poeze et al. |
| 10,383,520 B2 | 8/2019 | Wojtczuk et al. |
| 10,383,527 B2 | 8/2019 | Al-Ali |
| 10,388,120 B2 | 8/2019 | Muhsin et al. |
| 10,398,320 B2 | 9/2019 | Kiani et al. |
| 10,405,804 B2 | 9/2019 | Al-Ali |
| 10,413,666 B2 | 9/2019 | Al-Ali et al. |
| 10,420,493 B2 | 9/2019 | Al-Ali et al. |
| D864,120 S | 10/2019 | Forrest et al. |
| 10,441,181 B1 | 10/2019 | Telfort et al. |
| 10,441,196 B2 | 10/2019 | Eckerbom et al. |
| 10,448,844 B2 | 10/2019 | Al-Ali et al. |
| 10,448,871 B2 | 10/2019 | Al-Ali et al. |
| 10,456,038 B2 | 10/2019 | Lamego et al. |
| 10,463,340 B2 | 11/2019 | Telfort et al. |
| 10,471,159 B1 | 11/2019 | Lapotko et al. |
| 10,505,311 B2 | 12/2019 | Al-Ali et al. |
| 10,524,738 B2 | 1/2020 | Olsen |
| 10,532,174 B2 | 1/2020 | Al-Ali |
| 10,537,285 B2 | 1/2020 | Shreim et al. |
| 10,542,903 B2 | 1/2020 | Al-Ali et al. |
| 10,555,678 B2 | 2/2020 | Dalvi et al. |

(56) References Cited

U.S. PATENT DOCUMENTS

| | | |
|---|---|---|
| 10,568,553 B2 | 2/2020 | O'Neil et al. |
| RE47,882 E | 3/2020 | Al-Ali |
| 10,608,817 B2 | 3/2020 | Haider et al. |
| D880,477 S | 4/2020 | Forrest et al. |
| 10,617,302 B2 | 4/2020 | Al-Ali et al. |
| 10,617,335 B2 | 4/2020 | Al-Ali et al. |
| 10,637,181 B2 | 4/2020 | Al-Ali et al. |
| D887,548 S | 6/2020 | Abdul-Hafiz et al. |
| D887,549 S | 6/2020 | Abdul-Hafiz et al. |
| 10,667,764 B2 | 6/2020 | Ahmed et al. |
| D890,708 S | 7/2020 | Forrest et al. |
| 10,721,785 B2 | 7/2020 | Al-Ali |
| 10,736,518 B2 | 8/2020 | Al-Ali et al. |
| 10,750,984 B2 | 8/2020 | Pauley et al. |
| D897,098 S | 9/2020 | Al-Ali |
| 10,779,098 B2 | 9/2020 | Iswanto et al. |
| 10,827,961 B1 | 11/2020 | Iyengar et al. |
| 10,828,007 B1 | 11/2020 | Telfort et al. |
| 10,832,818 B2 | 11/2020 | Muhsin et al. |
| 10,849,554 B2 | 12/2020 | Shreim et al. |
| 10,856,750 B2 | 12/2020 | Indorf et al. |
| D906,970 S | 1/2021 | Forrest et al. |
| 10,918,281 B2 | 2/2021 | Al-Ali et al. |
| 10,932,705 B2 | 3/2021 | Muhsin et al. |
| 10,932,729 B2 | 3/2021 | Kiani et al. |
| 10,939,878 B2 | 3/2021 | Kiani et al. |
| 10,956,950 B2 | 3/2021 | Al-Ali et al. |
| D916,135 S | 4/2021 | Indorf et al. |
| D917,550 S | 4/2021 | Indorf et al. |
| D917,564 S | 4/2021 | Indorf et al. |
| D917,704 S | 4/2021 | Al-Ali et al. |
| 10,987,066 B2 | 4/2021 | Chandran et al. |
| 10,991,135 B2 | 4/2021 | Al-Ali et al. |
| D919,094 S | 5/2021 | Al-Ali et al. |
| D919,100 S | 5/2021 | Al-Ali et al. |
| 11,006,867 B2 | 5/2021 | Al-Ali |
| D921,202 S | 6/2021 | Al-Ali et al. |
| 11,024,064 B2 | 6/2021 | Muhsin et al. |
| 11,026,604 B2 | 6/2021 | Chen et al. |
| D925,597 S | 7/2021 | Chandran et al. |
| D927,699 S | 8/2021 | Al-Ali et al. |
| 11,076,777 B2 | 8/2021 | Lee et al. |
| 11,114,188 B2 | 9/2021 | Poeze et al. |
| D933,232 S | 10/2021 | Al-Ali et al. |
| 11,145,408 B2 | 10/2021 | Sampath et al. |
| 11,147,518 B1 | 10/2021 | Al-Ali et al. |
| 11,185,262 B2 | 11/2021 | Al-Ali et al. |
| 11,191,484 B2 | 12/2021 | Kiani et al. |
| 2001/0034477 A1 | 10/2001 | Mansfield et al. |
| 2001/0039483 A1 | 11/2001 | Brand et al. |
| 2002/0010401 A1 | 1/2002 | Bushmakin et al. |
| 2002/0058864 A1 | 5/2002 | Mansfield et al. |
| 2002/0133080 A1 | 9/2002 | Apruzzese et al. |
| 2003/0013975 A1 | 1/2003 | Kiani |
| 2003/0018243 A1 | 1/2003 | Gerhardt et al. |
| 2003/0144582 A1 | 7/2003 | Cohen et al. |
| 2003/0156288 A1 | 8/2003 | Barnum et al. |
| 2003/0212312 A1 | 11/2003 | Coffin, IV et al. |
| 2004/0106163 A1 | 6/2004 | Workman, Jr. et al. |
| 2005/0055276 A1 | 3/2005 | Kiani et al. |
| 2005/0234317 A1 | 10/2005 | Kiani |
| 2006/0073719 A1 | 4/2006 | Kiani |
| 2006/0161054 A1 | 7/2006 | Reuss et al. |
| 2006/0189871 A1 | 8/2006 | Al-Ali et al. |
| 2007/0073116 A1 | 3/2007 | Kiani et al. |
| 2007/0180140 A1 | 8/2007 | Welch et al. |
| 2007/0244377 A1 | 10/2007 | Cozad et al. |
| 2007/0282478 A1 | 12/2007 | Al-Ali et al. |
| 2008/0064965 A1 | 3/2008 | Jay et al. |
| 2008/0094228 A1 | 4/2008 | Welch et al. |
| 2008/0221418 A1 | 9/2008 | Al-Ali et al. |
| 2009/0036759 A1 | 2/2009 | Ault et al. |
| 2009/0093687 A1 | 4/2009 | Telfort et al. |
| 2009/0095926 A1 | 4/2009 | MacNeish, III |
| 2009/0247984 A1 | 10/2009 | Lamego et al. |
| 2009/0275813 A1 | 11/2009 | Davis |
| 2009/0275844 A1 | 11/2009 | Al-Ali |
| 2010/0004518 A1 | 1/2010 | Vo et al. |
| 2010/0030040 A1 | 2/2010 | Poeze et al. |
| 2010/0099964 A1 | 4/2010 | O'Reilly et al. |
| 2010/0234718 A1 | 9/2010 | Sampath et al. |
| 2010/0270257 A1 | 10/2010 | Wachman et al. |
| 2011/0028806 A1 | 2/2011 | Merritt et al. |
| 2011/0028809 A1 | 2/2011 | Goodman |
| 2011/0040197 A1 | 2/2011 | Welch et al. |
| 2011/0082711 A1 | 4/2011 | Poeze et al. |
| 2011/0087081 A1 | 4/2011 | Kiani et al. |
| 2011/0112387 A1* | 5/2011 | Li .................. A61B 5/14551 600/324 |
| 2011/0118561 A1 | 5/2011 | Tari et al. |
| 2011/0125060 A1 | 5/2011 | Telfort et al. |
| 2011/0137297 A1 | 6/2011 | Kiani et al. |
| 2011/0172498 A1 | 7/2011 | Olsen et al. |
| 2011/0208015 A1 | 8/2011 | Welch et al. |
| 2011/0230733 A1 | 9/2011 | Al-Ali |
| 2012/0123231 A1 | 5/2012 | O'Reilly |
| 2012/0165629 A1 | 6/2012 | Merritt et al. |
| 2012/0209082 A1 | 8/2012 | Al-Ali |
| 2012/0209084 A1 | 8/2012 | Olsen et al. |
| 2012/0226117 A1 | 9/2012 | Lamego et al. |
| 2012/0283524 A1 | 11/2012 | Kiani et al. |
| 2013/0023775 A1 | 1/2013 | Lamego et al. |
| 2013/0041591 A1 | 2/2013 | Lamego |
| 2013/0060147 A1 | 3/2013 | Welch et al. |
| 2013/0096405 A1 | 4/2013 | Garfio |
| 2013/0096936 A1 | 4/2013 | Sampath et al. |
| 2013/0243021 A1 | 9/2013 | Siskavich |
| 2013/0253334 A1 | 9/2013 | Al-Ali et al. |
| 2013/0296672 A1 | 11/2013 | O'Neil et al. |
| 2013/0296713 A1 | 11/2013 | Al-Ali et al. |
| 2013/0324808 A1 | 12/2013 | Al-Ali et al. |
| 2013/0331660 A1 | 12/2013 | Al-Ali et al. |
| 2013/0345921 A1 | 12/2013 | Al-Ali et al. |
| 2014/0012100 A1 | 1/2014 | Al-Ali et al. |
| 2014/0051953 A1 | 2/2014 | Lamego et al. |
| 2014/0120564 A1 | 5/2014 | Workman et al. |
| 2014/0121482 A1 | 5/2014 | Merritt et al. |
| 2014/0127137 A1 | 5/2014 | Bellott et al. |
| 2014/0163344 A1 | 6/2014 | Al-Ali |
| 2014/0166076 A1 | 6/2014 | Kiani et al. |
| 2014/0171763 A1 | 6/2014 | Diab |
| 2014/0180038 A1 | 6/2014 | Kiani |
| 2014/0180154 A1 | 6/2014 | Sierra et al. |
| 2014/0180160 A1 | 6/2014 | Brown et al. |
| 2014/0187973 A1 | 7/2014 | Brown et al. |
| 2014/0213864 A1 | 7/2014 | Abdul-Hafiz et al. |
| 2014/0275835 A1 | 9/2014 | Lamego et al. |
| 2014/0275871 A1 | 9/2014 | Lamego et al. |
| 2014/0275872 A1 | 9/2014 | Merritt et al. |
| 2014/0288400 A1 | 9/2014 | Diab et al. |
| 2014/0316217 A1 | 10/2014 | Purdon et al. |
| 2014/0316218 A1 | 10/2014 | Purdon et al. |
| 2014/0316228 A1 | 10/2014 | Blank et al. |
| 2014/0323825 A1 | 10/2014 | Al-Ali et al. |
| 2014/0323897 A1 | 10/2014 | Brown et al. |
| 2014/0323898 A1 | 10/2014 | Purdon et al. |
| 2014/0330092 A1 | 11/2014 | Al-Ali et al. |
| 2014/0330098 A1 | 11/2014 | Merritt et al. |
| 2014/0357966 A1 | 12/2014 | Al-Ali et al. |
| 2015/0005600 A1 | 1/2015 | Blank et al. |
| 2015/0011907 A1 | 1/2015 | Purdon et al. |
| 2015/0032029 A1 | 1/2015 | Al-Ali et al. |
| 2015/0038859 A1 | 2/2015 | Dalvi et al. |
| 2015/0073241 A1 | 3/2015 | Lamego |
| 2015/0080754 A1 | 3/2015 | Purdon et al. |
| 2015/0087936 A1 | 3/2015 | Al-Ali et al. |
| 2015/0094546 A1 | 4/2015 | Al-Ali |
| 2015/0099950 A1 | 4/2015 | Al-Ali et al. |
| 2015/0101844 A1 | 4/2015 | Al-Ali et al. |
| 2015/0106121 A1 | 4/2015 | Muhsin et al. |
| 2015/0112151 A1 | 4/2015 | Muhsin et al. |
| 2015/0165312 A1 | 6/2015 | Kiani |
| 2015/0196249 A1 | 7/2015 | Brown et al. |
| 2015/0216459 A1 | 8/2015 | Al-Ali et al. |

(56) References Cited

U.S. PATENT DOCUMENTS

| | | |
|---|---|---|
| 2015/0238722 A1 | 8/2015 | Al-Ali |
| 2015/0245773 A1 | 9/2015 | Lamego et al. |
| 2015/0245794 A1 | 9/2015 | Al-Ali |
| 2015/0257689 A1 | 9/2015 | Al-Ali et al. |
| 2015/0272514 A1 | 10/2015 | Kiani et al. |
| 2015/0351697 A1 | 12/2015 | Weber et al. |
| 2015/0359429 A1 | 12/2015 | Al-Ali et al. |
| 2015/0366507 A1 | 12/2015 | Blank |
| 2016/0029932 A1 | 2/2016 | Al-Ali |
| 2016/0058347 A1 | 3/2016 | Reichgott et al. |
| 2016/0066824 A1 | 3/2016 | Al-Ali et al. |
| 2016/0081552 A1 | 3/2016 | Wojtczuk et al. |
| 2016/0095543 A1 | 4/2016 | Telfort et al. |
| 2016/0095548 A1 | 4/2016 | Al-Ali et al. |
| 2016/0103598 A1 | 4/2016 | Al-Ali et al. |
| 2016/0166182 A1 | 6/2016 | Al-Ali et al. |
| 2016/0166183 A1 | 6/2016 | Poeze et al. |
| 2016/0196388 A1 | 7/2016 | Lamego |
| 2016/0197436 A1 | 7/2016 | Barker et al. |
| 2016/0213281 A1 | 7/2016 | Eckerbom et al. |
| 2016/0228043 A1 | 8/2016 | O'Neil et al. |
| 2016/0233632 A1 | 8/2016 | Scruggs et al. |
| 2016/0234944 A1 | 8/2016 | Schmidt et al. |
| 2016/0270735 A1 | 9/2016 | Diab et al. |
| 2016/0283665 A1 | 9/2016 | Sampath et al. |
| 2016/0287090 A1 | 10/2016 | Al-Ali et al. |
| 2016/0287786 A1 | 10/2016 | Kiani |
| 2016/0296169 A1 | 10/2016 | McHale et al. |
| 2016/0310052 A1 | 10/2016 | Al-Ali et al. |
| 2016/0314260 A1 | 10/2016 | Kiani |
| 2016/0324488 A1 | 11/2016 | Olsen |
| 2016/0327984 A1 | 11/2016 | Al-Ali et al. |
| 2016/0331332 A1 | 11/2016 | Al-Ali |
| 2016/0367173 A1 | 12/2016 | Dalvi et al. |
| 2017/0000394 A1 | 1/2017 | Al-Ali et al. |
| 2017/0007134 A1 | 1/2017 | Al-Ali et al. |
| 2017/0007198 A1 | 1/2017 | Al-Ali et al. |
| 2017/0014083 A1 | 1/2017 | Diab et al. |
| 2017/0014084 A1 | 1/2017 | Al-Ali et al. |
| 2017/0024748 A1 | 1/2017 | Haider |
| 2017/0042488 A1 | 2/2017 | Muhsin |
| 2017/0055851 A1 | 3/2017 | Al-Ali |
| 2017/0055882 A1 | 3/2017 | Al-Ali et al. |
| 2017/0055887 A1 | 3/2017 | Al-Ali |
| 2017/0055896 A1 | 3/2017 | Al-Ali et al. |
| 2017/0079594 A1 | 3/2017 | Telfort et al. |
| 2017/0086723 A1 | 3/2017 | Al-Ali et al. |
| 2017/0143281 A1 | 5/2017 | Olsen |
| 2017/0147774 A1 | 5/2017 | Kiani |
| 2017/0156620 A1 | 6/2017 | Al-Ali et al. |
| 2017/0173632 A1 | 6/2017 | Al-Ali |
| 2017/0187146 A1 | 6/2017 | Kiani et al. |
| 2017/0188919 A1 | 7/2017 | Al-Ali et al. |
| 2017/0196464 A1 | 7/2017 | Jansen et al. |
| 2017/0196470 A1 | 7/2017 | Lamego et al. |
| 2017/0224262 A1 | 8/2017 | Al-Ali |
| 2017/0228516 A1 | 8/2017 | Sampath et al. |
| 2017/0245790 A1 | 8/2017 | Al-Ali et al. |
| 2017/0251974 A1 | 9/2017 | Shreim et al. |
| 2017/0251975 A1 | 9/2017 | Shreim et al. |
| 2017/0258403 A1 | 9/2017 | Abdul-Hafiz et al. |
| 2017/0311851 A1 | 11/2017 | Schurman et al. |
| 2017/0311891 A1 | 11/2017 | Kiani et al. |
| 2017/0325728 A1 | 11/2017 | Al-Ali et al. |
| 2017/0332976 A1 | 11/2017 | Al-Ali et al. |
| 2017/0340293 A1 | 11/2017 | Al-Ali et al. |
| 2017/0360310 A1 | 12/2017 | Kiani et al. |
| 2017/0367632 A1 | 12/2017 | Al-Ali et al. |
| 2018/0008146 A1 | 1/2018 | Al-Ali et al. |
| 2018/0013562 A1 | 1/2018 | Haider et al. |
| 2018/0014752 A1 | 1/2018 | Al-Ali et al. |
| 2018/0028124 A1 | 2/2018 | Al-Ali et al. |
| 2018/0055385 A1 | 3/2018 | Al-Ali |
| 2018/0055390 A1 | 3/2018 | Kiani et al. |
| 2018/0055430 A1 | 3/2018 | Diab et al. |
| 2018/0064381 A1 | 3/2018 | Shakespeare et al. |
| 2018/0069776 A1 | 3/2018 | Lamego et al. |
| 2018/0070867 A1 | 3/2018 | Smith et al. |
| 2018/0082767 A1 | 3/2018 | Al-Ali et al. |
| 2018/0085068 A1 | 3/2018 | Telfort |
| 2018/0087937 A1 | 3/2018 | Al-Ali et al. |
| 2018/0103874 A1 | 4/2018 | Lee et al. |
| 2018/0103905 A1 | 4/2018 | Kiani |
| 2018/0110478 A1 | 4/2018 | Al-Ali |
| 2018/0116575 A1 | 5/2018 | Perea et al. |
| 2018/0125368 A1 | 5/2018 | Lamego et al. |
| 2018/0125430 A1 | 5/2018 | Al-Ali et al. |
| 2018/0125445 A1 | 5/2018 | Telfort et al. |
| 2018/0130325 A1 | 5/2018 | Kiani et al. |
| 2018/0132769 A1 | 5/2018 | Weber et al. |
| 2018/0132770 A1 | 5/2018 | Lamego |
| 2018/0146901 A1 | 5/2018 | Al-Ali et al. |
| 2018/0146902 A1 | 5/2018 | Kiani et al. |
| 2018/0153442 A1 | 6/2018 | Eckerbom et al. |
| 2018/0153446 A1 | 6/2018 | Kiani |
| 2018/0153447 A1 | 6/2018 | Al-Ali et al. |
| 2018/0153448 A1 | 6/2018 | Weber et al. |
| 2018/0161499 A1 | 6/2018 | Al-Ali et al. |
| 2018/0168491 A1 | 6/2018 | Al-Ali et al. |
| 2018/0174679 A1 | 6/2018 | Sampath et al. |
| 2018/0174680 A1 | 6/2018 | Sampath et al. |
| 2018/0182484 A1 | 6/2018 | Sampath et al. |
| 2018/0184917 A1 | 7/2018 | Kiani |
| 2018/0192924 A1 | 7/2018 | Al-Ali |
| 2018/0192953 A1 | 7/2018 | Shreim et al. |
| 2018/0192955 A1 | 7/2018 | Al-Ali et al. |
| 2018/0199871 A1 | 7/2018 | Pauley et al. |
| 2018/0206795 A1 | 7/2018 | Al-Ali |
| 2018/0206815 A1 | 7/2018 | Telfort |
| 2018/0213583 A1 | 7/2018 | Al-Ali |
| 2018/0214031 A1 | 8/2018 | Kiani et al. |
| 2018/0214090 A1 | 8/2018 | Al-Ali et al. |
| 2018/0216370 A1 | 8/2018 | Ishiguro et al. |
| 2018/0218792 A1 | 8/2018 | Muhsin et al. |
| 2018/0225960 A1 | 8/2018 | Al-Ali et al. |
| 2018/0238718 A1 | 8/2018 | Dalvi |
| 2018/0242853 A1 | 8/2018 | Al-Ali |
| 2018/0242921 A1 | 8/2018 | Muhsin et al. |
| 2018/0242923 A1 | 8/2018 | Al-Ali et al. |
| 2018/0242924 A1 | 8/2018 | Barker et al. |
| 2018/0242926 A1 | 8/2018 | Muhsin et al. |
| 2018/0247353 A1 | 8/2018 | Al-Ali et al. |
| 2018/0247712 A1 | 8/2018 | Muhsin et al. |
| 2018/0249933 A1 | 9/2018 | Schurman et al. |
| 2018/0253947 A1 | 9/2018 | Muhsin et al. |
| 2018/0256087 A1 | 9/2018 | Al-Ali et al. |
| 2018/0256113 A1 | 9/2018 | Weber et al. |
| 2018/0285094 A1 | 10/2018 | Housel et al. |
| 2018/0289325 A1 | 10/2018 | Poeze et al. |
| 2018/0289337 A1 | 10/2018 | Al-Ali et al. |
| 2018/0296161 A1 | 10/2018 | Shreim et al. |
| 2018/0300919 A1 | 10/2018 | Muhsin et al. |
| 2018/0310822 A1 | 11/2018 | Indorf et al. |
| 2018/0310823 A1 | 11/2018 | Al-Ali et al. |
| 2018/0317826 A1 | 11/2018 | Muhsin |
| 2018/0317841 A1 | 11/2018 | Novak, Jr. |
| 2018/0333055 A1 | 11/2018 | Lamego et al. |
| 2018/0333087 A1 | 11/2018 | Al-Ali |
| 2019/0000317 A1 | 1/2019 | Muhsin et al. |
| 2019/0000362 A1 | 1/2019 | Kiani et al. |
| 2019/0015023 A1 | 1/2019 | Monfre |
| 2019/0021638 A1 | 1/2019 | Al-Ali et al. |
| 2019/0029574 A1 | 1/2019 | Schurman et al. |
| 2019/0029578 A1 | 1/2019 | Al-Ali et al. |
| 2019/0038143 A1 | 2/2019 | Al-Ali |
| 2019/0058280 A1 | 2/2019 | Al-Ali et al. |
| 2019/0058281 A1 | 2/2019 | Al-Ali et al. |
| 2019/0069813 A1 | 3/2019 | Al-Ali |
| 2019/0069814 A1 | 3/2019 | Al-Ali |
| 2019/0076028 A1 | 3/2019 | Al-Ali et al. |
| 2019/0082979 A1 | 3/2019 | Al-Ali et al. |
| 2019/0090748 A1 | 3/2019 | Al-Ali |
| 2019/0090760 A1 | 3/2019 | Kinast et al. |
| 2019/0090764 A1 | 3/2019 | Al-Ali |

(56) References Cited

U.S. PATENT DOCUMENTS

| | | |
|---|---|---|
| 2019/0104973 A1 | 4/2019 | Poeze et al. |
| 2019/0110719 A1 | 4/2019 | Poeze et al. |
| 2019/0117070 A1 | 4/2019 | Muhsin et al. |
| 2019/0117139 A1 | 4/2019 | Al-Ali et al. |
| 2019/0117140 A1 | 4/2019 | Al-Ali et al. |
| 2019/0117141 A1 | 4/2019 | Al-Ali |
| 2019/0117930 A1 | 4/2019 | Al-Ali |
| 2019/0122763 A1 | 4/2019 | Sampath et al. |
| 2019/0133525 A1 | 5/2019 | Al-Ali et al. |
| 2019/0142283 A1 | 5/2019 | Lamego et al. |
| 2019/0142344 A1 | 5/2019 | Telfort et al. |
| 2019/0150800 A1 | 5/2019 | Poeze et al. |
| 2019/0150856 A1 | 5/2019 | Kiani et al. |
| 2019/0167161 A1 | 6/2019 | Al-Ali et al. |
| 2019/0175019 A1 | 6/2019 | Al-Ali et al. |
| 2019/0192076 A1 | 6/2019 | McHale et al. |
| 2019/0200941 A1 | 7/2019 | Chandran et al. |
| 2019/0201623 A1 | 7/2019 | Kiani |
| 2019/0209025 A1 | 7/2019 | Al-Ali |
| 2019/0214778 A1 | 7/2019 | Scruggs et al. |
| 2019/0216319 A1 | 7/2019 | Poeze et al. |
| 2019/0216379 A1 | 7/2019 | Al-Ali et al. |
| 2019/0221966 A1 | 7/2019 | Kiani et al. |
| 2019/0223804 A1 | 7/2019 | Blank et al. |
| 2019/0231199 A1 | 8/2019 | Al-Ali et al. |
| 2019/0231241 A1 | 8/2019 | Al-Ali et al. |
| 2019/0231270 A1 | 8/2019 | Abdul-Hafiz et al. |
| 2019/0239787 A1 | 8/2019 | Pauley et al. |
| 2019/0239824 A1 | 8/2019 | Muhsin et al. |
| 2019/0254578 A1 | 8/2019 | Lamego |
| 2019/0261857 A1 | 8/2019 | Al-Ali |
| 2019/0269370 A1 | 9/2019 | Al-Ali et al. |
| 2019/0274606 A1 | 9/2019 | Kiani et al. |
| 2019/0274627 A1 | 9/2019 | Al-Ali et al. |
| 2019/0274635 A1 | 9/2019 | Al-Ali et al. |
| 2019/0290136 A1 | 9/2019 | Dalvi et al. |
| 2019/0298270 A1 | 10/2019 | Al-Ali et al. |
| 2019/0304601 A1 | 10/2019 | Sampath et al. |
| 2019/0304605 A1 | 10/2019 | Al-Ali |
| 2019/0320906 A1 | 10/2019 | Olsen |
| 2019/0374713 A1 | 12/2019 | Kiani et al. |
| 2020/0060869 A1 | 2/2020 | Telfort et al. |
| 2020/0111552 A1 | 4/2020 | Ahmed |
| 2020/0113435 A1 | 4/2020 | Muhsin |
| 2020/0113488 A1 | 4/2020 | Al-Ali et al. |
| 2020/0113496 A1 | 4/2020 | Scruggs et al. |
| 2020/0113520 A1 | 4/2020 | Abdul-Hafiz et al. |
| 2020/0138288 A1 | 5/2020 | Al-Ali et al. |
| 2020/0138368 A1 | 5/2020 | Kiani et al. |
| 2020/0163597 A1 | 5/2020 | Dalvi et al. |
| 2020/0196877 A1 | 6/2020 | Vo et al. |
| 2020/0253474 A1 | 8/2020 | Muhsin et al. |
| 2020/0253544 A1 | 8/2020 | Belur Nagaraj et al. |
| 2020/0275841 A1 | 9/2020 | Telfort et al. |
| 2020/0288983 A1 | 9/2020 | Telfort et al. |
| 2020/0321793 A1 | 10/2020 | Al-Ali et al. |
| 2020/0329983 A1 | 10/2020 | Al-Ali et al. |
| 2020/0329984 A1 | 10/2020 | Al-Ali et al. |
| 2020/0329993 A1 | 10/2020 | Al-Ali et al. |
| 2020/0330037 A1 | 10/2020 | Al-Ali et al. |
| 2021/0022628 A1 | 1/2021 | Telfort et al. |
| 2021/0104173 A1 | 4/2021 | Pauley et al. |
| 2021/0113121 A1 | 4/2021 | Diab et al. |
| 2021/0117525 A1 | 4/2021 | Kiani et al. |
| 2021/0118581 A1 | 4/2021 | Kiani et al. |
| 2021/0121582 A1 | 4/2021 | Krishnamani et al. |
| 2021/0161465 A1 | 6/2021 | Barker et al. |
| 2021/0236729 A1 | 8/2021 | Kiani et al. |
| 2021/0256267 A1 | 8/2021 | Ranasinghe et al. |
| 2021/0256835 A1 | 8/2021 | Ranasinghe et al. |
| 2021/0275101 A1 | 9/2021 | Vo et al. |
| 2021/0290060 A1 | 9/2021 | Ahmed |
| 2021/0290072 A1 | 9/2021 | Forrest |
| 2021/0290080 A1 | 9/2021 | Ahmed |
| 2021/0290120 A1 | 9/2021 | Al-Ali |
| 2021/0290177 A1 | 9/2021 | Novak, Jr. |
| 2021/0290184 A1 | 9/2021 | Ahmed |
| 2021/0296008 A1 | 9/2021 | Novak, Jr. |
| 2021/0330228 A1 | 10/2021 | Olsen et al. |
| 2021/0386382 A1 | 12/2021 | Olsen et al. |
| 2021/0402110 A1 | 12/2021 | Pauley et al. |

\* cited by examiner

LOW NOISE OXIMETRY CABLE

RELATED APPLICATIONS

Any and all applications for which a domestic priority claim is identified in the Application Data Sheet of the present application are hereby incorporated by reference under 37 CFR 1.57.

BACKGROUND

Field of the Disclosure

The disclosure relates to improving the performance of patient monitors through low noise cabling.

Description of the Related Art

Oximetry utilizes a noninvasive optical sensor to measure physiological parameters of a patient. In general, the sensor has light emitting diodes (LEDs) that transmit optical radiation into a tissue site and a detector that responds to the intensity of the optical radiation after absorption (for example, by transmission or transreflectance) by, for example, pulsatile arterial blood flowing within the tissue site. Based on this response, a processor determines measurements for oxygen saturation ($SpO_2$), pulse rate, plethysmograph waveforms, perfusion quality index (for example, an index that quantifies perfusion), assessments of other blood constituents, parameters or analytes, including for example, a percent value for arterial carbon monoxide saturation (HbCO), a percent value for methemoglobin saturation (a brownish-red form of hemoglobin that cannot function as an oxygen carrier) (HbMet), total hemoglobin (HbT), fractional $SpO_2$ ($SpaO_2$) or the like.

Additionally, caregivers often desire knowledge of $HbO_2$, Hb, blood glucose (HbGu), water, the presence or absence of therapeutic drugs (aspirin, Dapson, nitrates, or the like) or abusive/recreational drugs (methamphetamine, alcohol, steroids, or the like), concentrations of carbon dioxide ($CO_2$), oxygen ($O_2$), oxygen concentration, pH levels, bilirubin, perfusion quality, albumin, cyanmethemoglobin, and sulfhemoglobin (HbSulf), signal quality or the like.

It is noted that "oximetry" as used herein encompasses its broad ordinary meaning known to one of skill in the art, which includes at least those noninvasive procedures for measuring parameters of circulating blood through spectroscopy. Moreover, "plethysmograph" as used herein (commonly referred to as "photoplethysmograph"), encompasses its broad ordinary meaning known to one of skill in the art, which includes at least data representative of a change in the absorption of particular wavelengths of light as a function of the changes in body tissue resulting from pulsing blood.

Oximeters capable of reading many of the foregoing parameters during motion induced noise are available from Masimo Corporation of Irvine, Calif. Moreover, portable and other oximeters are disclosed in at least U.S. Pat. Nos. 6,770,028, 6,658,276, 6,157,850, 6,002,952, and 5,769,785, which are incorporated by reference herein, and others patent publications such as those listed at http://www.masimo.com/patents.htm. Such reading through motion oximeters have gained rapid acceptance in a wide variety of medical applications, including surgical wards, intensive care and neonatal units, general wards, home care, physical training, and virtually all types of monitoring scenarios.

The detectors of the noninvasive sensors read by many of the foregoing patient monitors generate one or more low-level signals that are susceptible to corruption from various noise, such as electromagnetic interference (EMI) and internal noise that originate in the sensor, cabling and monitors. One internal noise source is due to a triboelectric effect, which includes static charges that build when two materials rub together. For example, when a cable housing detector wires is flexed, impacted, or the like, the detector wires may rub together and triboelectric noise can be induced in the detector signal. These induced triboelectric noise spikes can be orders of magnitude larger than the desired low level detector signals.

To alleviate the buildup of triboelectric charges, low noise cable manufacturers included graphite coatings exterior to, for example, the cabling configured to communicate detector signals. However, the graphite gel used in the manufacturing process proved difficult to apply and remove. Because of these and other difficulties, manufacturers began substituting the graphite coatings with a coextruded conductive PVC sheath around, for example, their sensitive signal carrying cables.

SUMMARY

The present disclosure describes a low noise oximetry cable that provides an improved, flexible, and durable overall construction for various medical environments. The cable can be particularly useful in environments such as emergency medical situations (EMS), where cables can undergo a tremendous amount of stress, such as repeated winding and unwinding, that can cause kinks to develop leading to or creating an electrical short in the cables. The construction of the cable described herein can reduce damage resulting from stress like repeated winding and unwinding and prevent kinks from developing. The cable can be part of a patient monitoring system that transmits real-time patient data to individual or multiple integrated or non-integrated devices.

The cable can include multiple bundles of conductors. The bundles can evenly distribute stress exerted on the conductors or cords within the cable. The bundles may be wrapped or weaved around a core that is flexible and durable. Some or all of conductors may be assembled twisted or untwisted with one or more cords. The conductors may be assembled twisted or untwisted around one or more central cores or cords.

An oximetry system is disclosed that can acquire signals indicative of one or more physiological parameters of a patient. The oximetry system can include a noninvasive sensor including a detector configured to detect light attenuated by a body tissue and output a detector signal indicative of the light detected after attenuation by the body tissue. The oximetry system also includes a patient monitor configured to receive the detector signal and determine one or more physiological parameters the patient from the detector signal. The oximetry system additionally includes a cable having an outer jacket, an outer shield, a first bundle including wires, a second bundle including wires, and a core at least partially surrounded by the first bundle and the second bundle. The outer shield at least partially surrounds the first bundle and the second bundle, and the outer jacket at least partially surrounds the outer shield.

A cable is disclosed that can transmit signals for an oximetry system usable to determine of one or more physiological parameters of a patient. The cable can include a first bundle with wires. The cable also can include a second bundle with wires. The cable can additionally include a core at least partially surrounded by the first bundle and the second bundle.

In some embodiments, an oximetry system is disclosed that can acquire signals indicative of one or more physiological parameters of a patient. The oximetry system can include a noninvasive sensor, a patient monitor, and a cable. The noninvasive sensor can include a detector configured to detect light attenuated by a body tissue of a patient and output a detector signal indicative of the light detected after attenuation by the body tissue. The patient monitor can be configured to receive the detector signal and determine one or more physiological parameters for the patient from the detector signal. The cable can include an outer jacket, an outer shield, a first bundle, and a second bundle. The first bundle can include a first plurality of wires. The second bundle can include a second plurality of wires. The outer shield can at least partially surround the first bundle and the second bundle. The outer jacket can at least partially surround the outer shield.

The oximetry system of the preceding paragraph can include one or more of the following features: The noninvasive sensor can include a sensor housing configured to position an emitter and the detector proximate to the body tissue. The one or more physiological parameters can include an oxygen saturation and a pulse rate. The cable can include a core configured to reduce a tensile stress exerted on the cable and increase a durability of the cable. The core can be flexible. The first bundle and the second bundle can be twisted or weaved around the core. The first bundle can include a first shield at least partially surrounding the first plurality of wires. The cable can include a third bundle at least partially surrounded by the outer shield. The third bundle can include a third plurality of wires. The first bundle, the second bundle, and the third bundle can be twisted or weaved around a core. The first bundle and the second bundle may not be concentric with each other. The cable can include a core, and the first bundle and the second bundle may not be concentric with the core. The first bundle can include a different number of wires than the second bundle. The core can include a plurality of arcuate surfaces that contact the first bundle and the second bundle and limit an amount of contact between the first bundle and the second bundle. The plurality of arcuate surfaces can be formed at least partly by pressure from the first bundle and the second bundle on the core.

A method of manufacturing the oximetry system of preceding two paragraphs is additionally disclosed.

In some embodiments, a cable is disclosed that can transmit signals in an oximetry system. The cable can include a first bundle, a second bundle, and a core. The first bundle can include a first plurality of wires. The second bundle can include a second plurality of wires. The core can be configured to reduce a tensile stress exerted on the cable and increase a durability of the cable.

The cable of the preceding paragraph can include one or more of the following features: The first bundle and the second bundle can be twisted or weaved around the core. The first bundle can include a first shield at least partially surrounding the first plurality of wires. The second bundle can include a second shield at least partially surrounding the second plurality of wires. A third bundle that can be disposed within a jacket along with the first bundle and the second bundle. The first bundle and the second bundle may not be concentric with each other. The first bundle and the second bundle may not be concentric with the core. The core can define a central axis. The first bundle can include a different number of wires than the second bundle.

A method of manufacturing the cable of preceding two paragraphs is additionally disclosed.

In some embodiments, a method is disclosed for manufacturing a cable that can transmit signals in an oximetry system. The method can include: assembling a first bundle that can include a first plurality of wires; assembling a second bundle that can include a second plurality of wires; and placing, within a jacket, the first bundle and the second bundle adjacent to a core.

For purposes of summarizing the disclosure, certain aspects, advantages and novel features are discussed herein. It is to be understood that not necessarily all such aspects, advantages or features will be embodied in any particular embodiment of the invention and an artisan would recognize from the disclosure herein a myriad of combinations of such aspects, advantages or features.

DETAILED DESCRIPTION

Introduction

A low noise oximetry cable is provided that can communicate a low level sensitive signals between a sensor and a patient monitor. Wires or cords of the cable can be twisted within individual bundles. The individual bundles can be encased within an inner jacket that can reduce friction between different cable elements. The bundles can be encased at least partially by an inner shield that may reduce EMI between the bundles and crosstalk with other cables.

The bundles can be disposed within an outer jacket and an outer shield. The bundles can wrap around a core. The core can be placed in the center of the cable and surrounded by the bundles so that the core can absorb stress exerted on the cable and various cable elements. The core can be composed of a flexible or durable material. Two, three, four, or more bundles can wrap around the core.

A patient monitor usable with the cable disclosed herein is the Root® Platform, a patient monitoring and connectivity platform available from Masimo Corporation, Irvine, Calif. A mobile physiological parameter monitoring system usable with the cable is described in U.S. Pat. No. 9,436,645, issued on Sep. 6, 2016, titled "MEDICAL MONITORING HUB," the disclosure of which is hereby incorporated by reference in its entirety.

To facilitate a complete understanding of the disclosure, the remainder of the detailed description references the drawings, wherein like references number are references with numerals throughout.

Patient Monitoring System Environment

Figure 1:
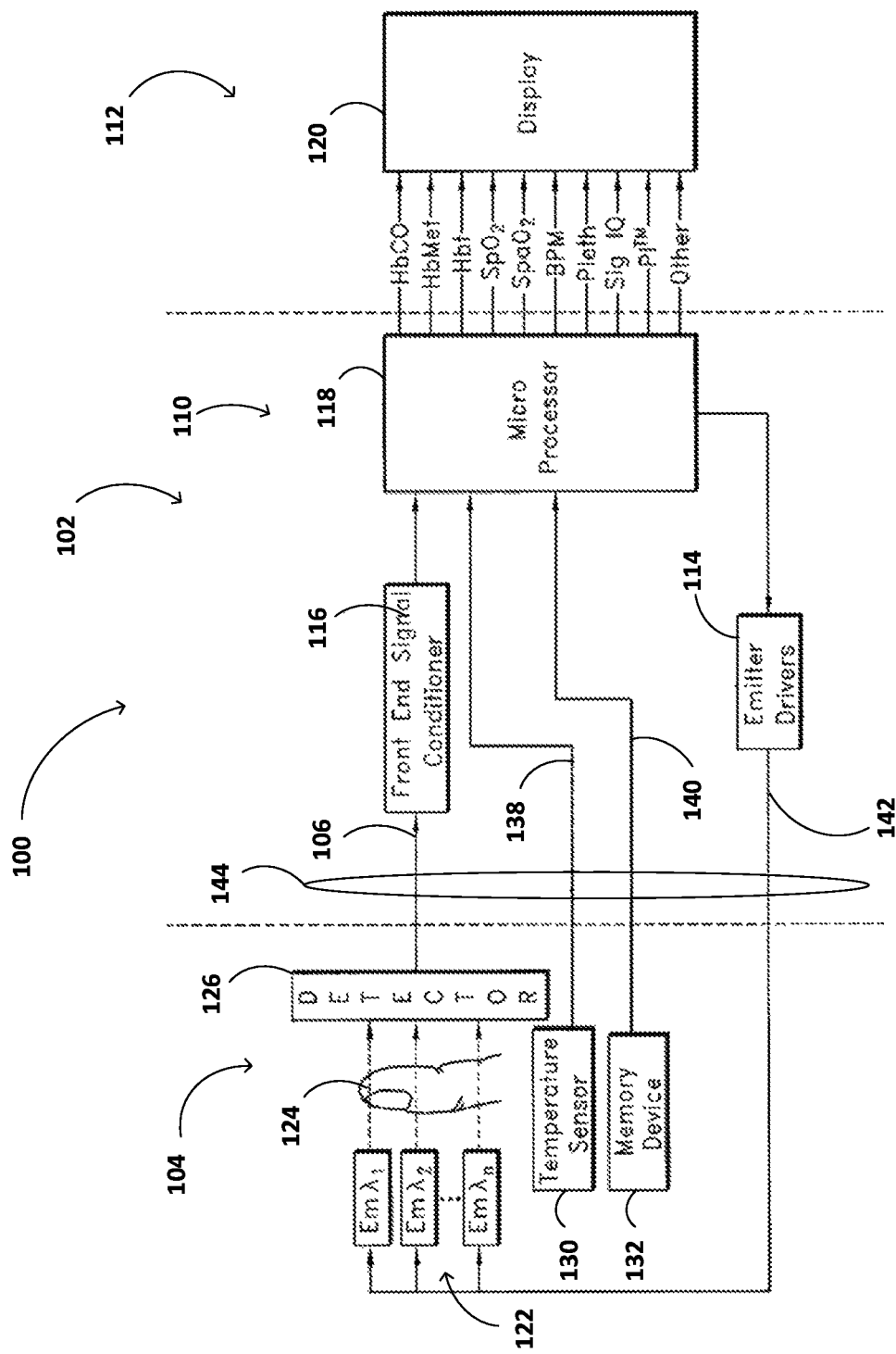
FIG. 1 is a block diagram of a patient monitoring system including a patient monitor and a noninvasive optical sensor communicating through a cable.

FIG. 1 illustrates a block diagram of a patient monitoring system 100 including a patient monitor 102 and a noninvasive optical sensor 104 communicating through a cable 144. The patient monitor 102 can include one or more processing boards 110 communicating with a host instrument 112. The one or more processing boards 110 can include processing circuitry arranged on one or more printed circuit boards capable of installation into a handheld or other monitor, or capable of being distributed as an OEM component for a wide variety of host instruments monitoring a wide variety of patient information. As shown, the one or more processing boards 110 can include an emitter driving circuit 114, a front end 116, and a microprocessor 118.

The emitter driving circuit 114 can output drive signals to the noninvasive optical sensor 104. The emitter driving circuit 114 may drive two (2) or more emitters capable of emitting light at two (2) or more wavelengths, or it may drive a matrix of eight (8) to sixteen (16) or more emitters capable of emitting light at eight (8) to sixteen (16) or more wavelengths.

The front end 116 can condition the signals, applies gain, converts signals to digital information, and the like, although any or all of the functions of the emitter driving circuit 114 and the front end 116 could be performed by other software or hardware components, or by the microprocessor 118. The microprocessor 118 may include one or more hardware or software components capable of executing instructions designed to control drive signals and to process incoming signal data related to the drive signals to determine desired physiological parameters of a monitored patient. Such parameters may include one or more of $SpO_2$, perfusion quality index, pulse rate, HbCO, HbMet, HbT, $SpaO_2$, $HbO_2$, Hb, HbGu, water, the presence or absence of therapeutic drugs or abusive/recreational drugs, $CO_2$, $O_2$, pH levels, bilirubin, albumin, cyanmethemoglobin, and HbSulf, signal quality, signal confidence measures, trend data on one, some, all, or combinations of the foregoing, or the like. Moreover, the microprocessor 118 can determine when alarm conditions exist for alerting a caregiver to the current condition of the patient.

The host instrument 112 can include a display device 120 capable of providing indicia representative of the calculated physiological parameters. The host instrument 112 can include virtually any housing, including a handheld or otherwise portable monitor capable of conveying one or more of the foregoing measured or calculated parameters to a caregiver. The host instrument 112 may include audio or visual alarms that alert caregivers that one or more physiological parameters are falling below or above predetermined safe thresholds, or are trending in a predetermined direction (good or bad). The host instrument 112 may include indications of the confidence a caregiver should have in the conveyed data.

The noninvasive optical sensor 104 can include emitters 122 irradiating a body tissue 124 with light, and one or more detectors 126 capable of detecting the light after attenuation by the body tissue 124. The noninvasive optical sensor 104 can also include a temperature sensor 130, such as, for example, a thermistor or the like, and a memory device 132. The memory device 132 may include any one or more of a wide variety of memory devices, including an EPROM, an EEPROM, a flash memory, a ROM, a RAM, single wire memories, combinations, or the like. The memory device 132 can store some or all of a wide variety data and information, including, for example, information on the type or operation of the sensor, type of patient or body tissue, buyer or manufacturer information, sensor characteristics including the number of wavelengths capable of being emitted, number of emitters, emitter specifications, emitter operational characteristics, emitter drive requirements, history of the sensor temperature, current, or voltage, demodulation data, calculation mode data, calibration data, software such as scripts, executable code, or the like, sensor electronic elements, sensor life data indicating whether some or all sensor components have expired and should be replaced, encryption information, keys, indexes to keys, the parameters the sensor is intended to measure (for example, HbCO, HbMet, etc.), monitor or algorithm upgrade instructions or data, some or all of parameter equations, combinations of the same, or the like.

As shown in FIG. 1, the cable 144 can communicate signals between the noninvasive optical sensor 104 and the one or more processing boards 110. The cable 144 can include one or more conductors including detector composite signal conductor(s) 106, temperature sensor conductor(s) 138, memory device conductor(s) 140, emitter drive signal conductor(s) 142, and the like. An example of the cable 144 is disclosed in U.S. Pat. No. 7,919,713, which is incorporated by reference herein.

Low-Noise Cable with Bundles

Figure 2A:
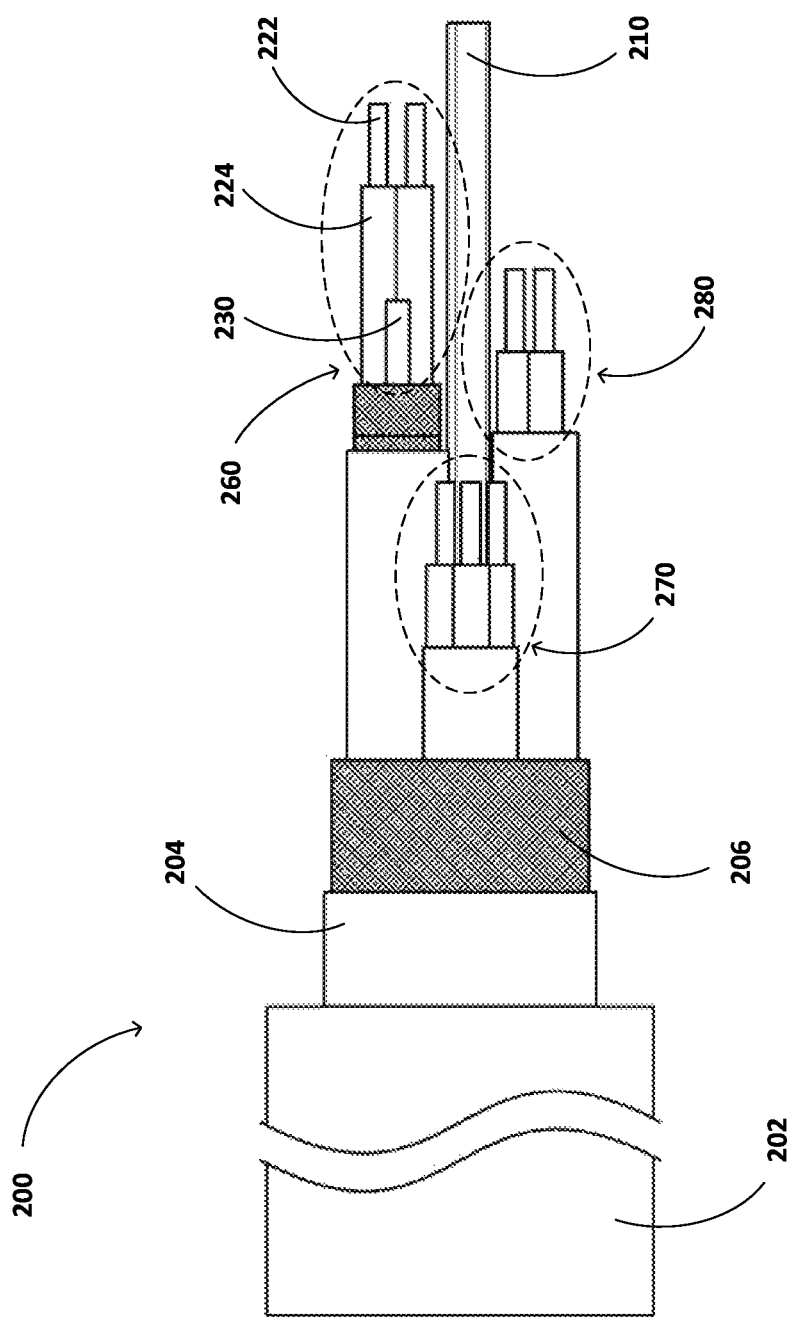
FIG. 2A is a cutaway side-view of the cable of FIG. 1.
Figure 2B:
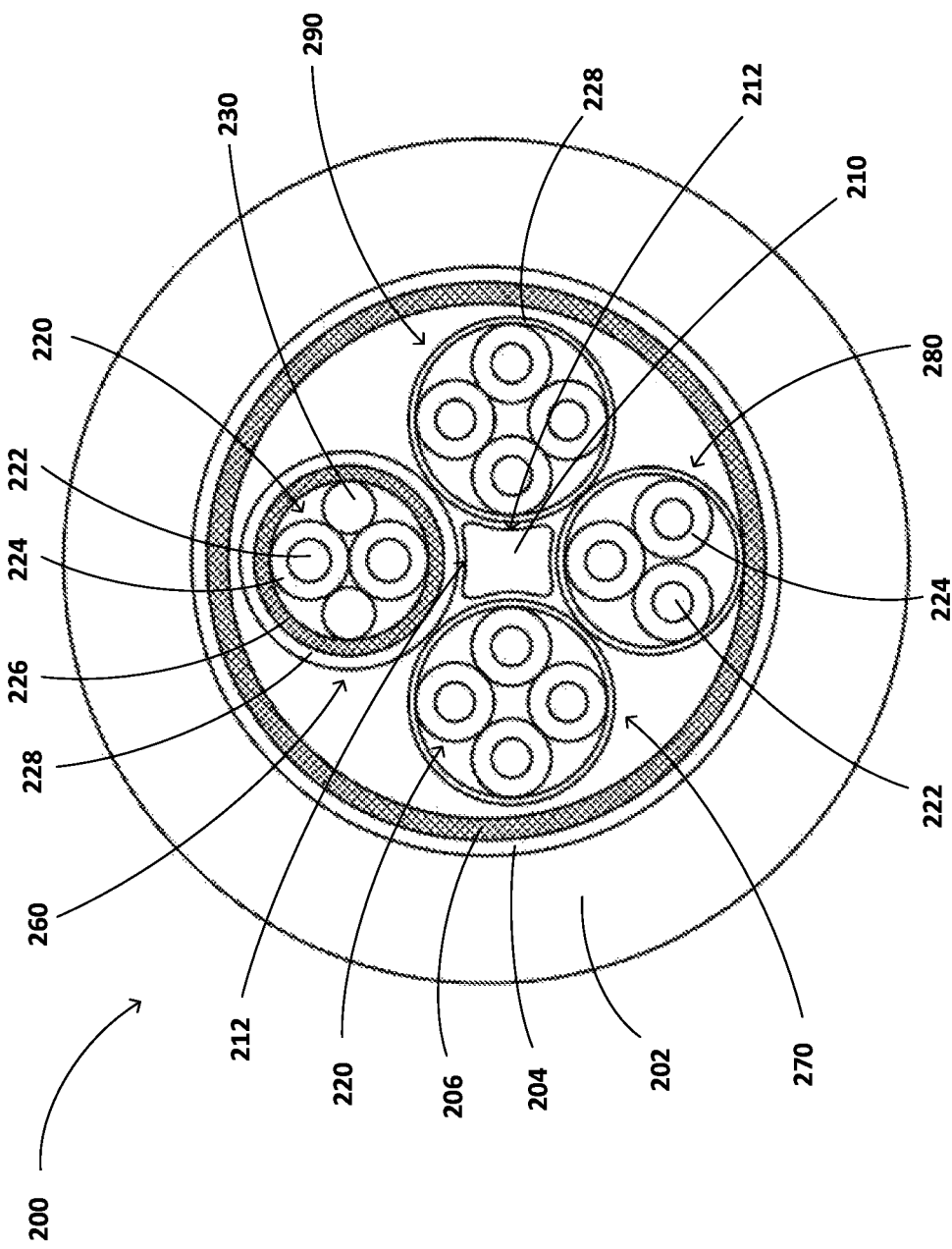
FIG. 2B is a cross-sectional view of the cable of FIG. 1.
Figure 2C:
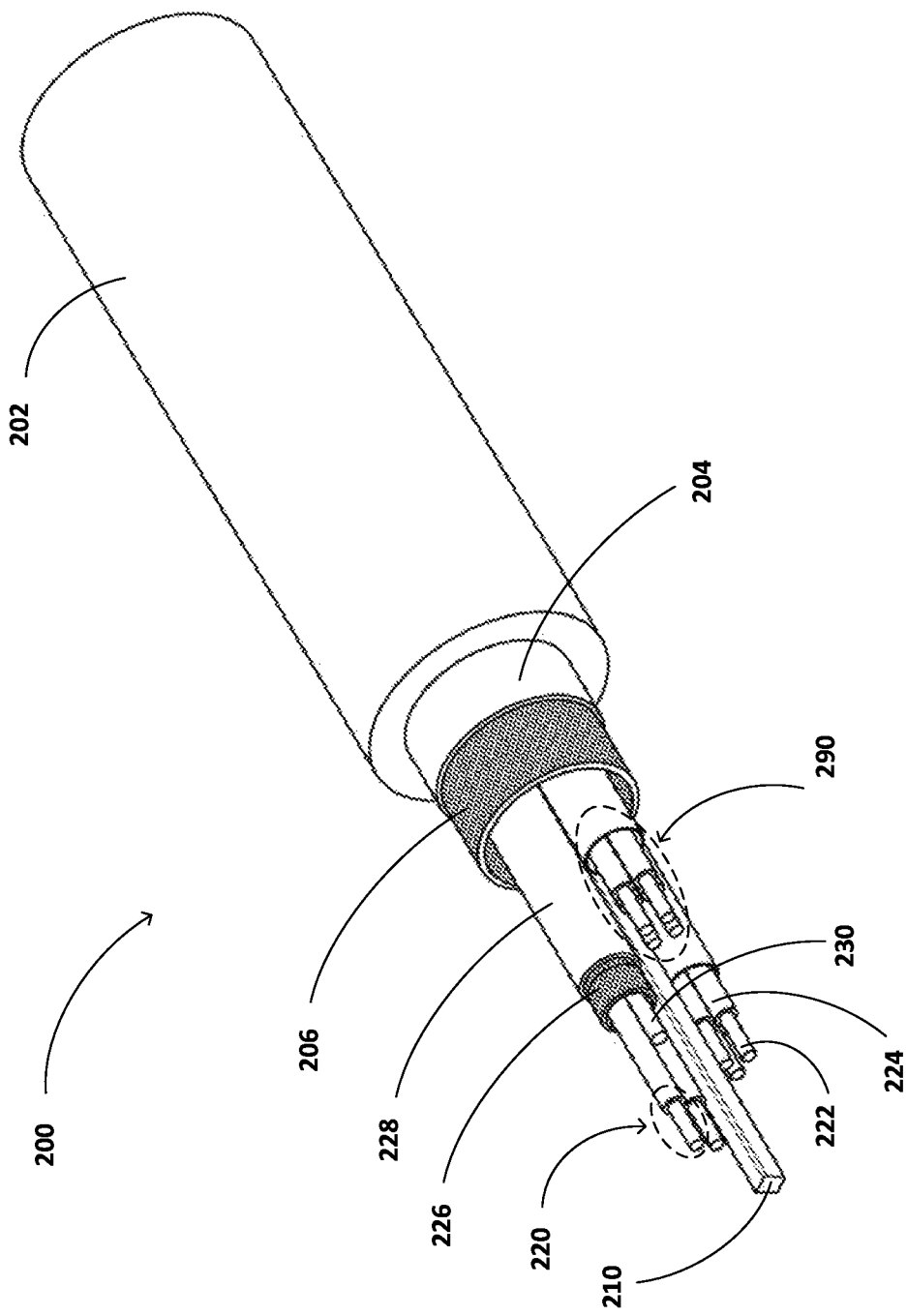
FIG. 2C is a cutaway perspective view of the cable of FIG. 1.

With reference to FIGS. 2A-2C, a patient cable 200 is disclosed. The cable 200 can be an example of the cable 144 of FIG. 1. The cable 200 can include an outer jacket 202, a separator 204, an outer shield 206, a first bundle 260, a second bundle 270, a third bundle 280, and a fourth bundle 290. The bundles 260, 270, 280, 290 can each include cords 230 or wires 220. The bundles 260, 270, 280, 290 can each include one or more cords 230 and one or more wires 220. The wires 220 can each include a conductor 222 encased by an insulator 224. The cable 200 can include a core 210 that is located adjacent to or between the bundles 260, 270, 280, 290.

The number of the bundles in the cable 200 can vary. The cable 200 can, for example, include two or three bundles instead of four. The number of the bundles in the cable 200 can vary depending upon desired cable thickness, shape, size (such as of an outer diameter), rigidity or flexibility, conductive performance, cost, number of signals transmitted, or the like.

The bundles 260, 270, 280, 290 can each include one or more of the wires 220. The number of the wires 220 in one of the bundles 260, 270, 280, 290 can vary depending upon desired bundle thickness, shape, size (such as outer diameter), rigidity or flexibility, conductive performance, cost, or the like. To give individual of the bundles 260, 270, 280, 290 a substantially circular shape while maintaining or improving triboelectric drain and substantially improving flexibility, the bundles 260, 270, 280, 290 can each include three or four of the wires 220 as shown in FIG. 2B. The bundles 260, 270, 280, 290 can alternatively each include two of the cords 230 and two of the wires 220. The bundles 260, 270, 280, 290 can alternatively each include five or more of the wires 220 or five or more of the cords 230. The total number of the wires 220 and the cords 230 in a given bundle can be more than four, five, six, seven, eight, nine, or ten.

The first bundle 260 can include two of the wires 220 and two of the cords 230, while the second bundle 270 and the fourth bundle 290 may each include four wires 220 but no cords 230. Moreover, the third bundle 280 may include three wires 220 and no cords 230. The total number of wires 220 or cords 230 can be the same or vary between one or more of the bundles 260, 270, 280, 290.

The cords 230 can each have an outer diameter ranging between about 0.015 inches and about 0.03 inches, between about 0.018 inches and about 0.028 inches, between about 0.02 inches and about 0.026 inches, between about 0.022 inches and about 0.024 inches, or about 0.015 inches, about 0.018 inches, about 0.02 inches, about 0.022 inches, about 0.024 inches, about 0.026 inches, about 0.028 inches, about 0.03 inches, or ranges between any two of aforementioned values. The outer diameter of each of the cords 230 can be less the about 0.015 inches or greater than about 0.03 inches. The cords 230 can each have an outer diameter of about 0.015 inches.

The wires 220 can each have an outer diameter ranging between about 0.02 inches and about 0.04 inches, between about 0.022 inches and about 0.038 inches, between about 0.024 inches and about 0.036 inches, between about 0.026 inches and about 0.034 inches, between about 0.028 inches and about 0.032 inches, or about 0.02 inches, about 0.022 inches, about 0.024 inches, about 0.026 inches, about 0.028 inches, about 0.03 inches, about 0.032 inches, about 0.034 inches, about 0.036 inches, about 0.038 inches, about 0.04 inches, or ranges between any two of aforementioned values. The outer diameter of each of the wires 220 can be less than about 0.02 inches or greater than about 0.04 inches. The wires 220 can each have an outer diameter of about 0.022 inches.

The bundles 260, 270, 280, 290 can each have a circumferential width ranging between about 0.04 inches and about 0.07 inches, about 0.045 inches and about 0.065 inches, about 0.05 inches and about 0.06 inches, about 0.054 inches and about 0.056 inches, or about 0.04 inches, about 0.045 inches, about 0.05 inches, about 0.055 inches, about 0.06 inches, about 0.065 inches, about 0.07 inches, or ranges between any two of aforementioned values. The circumferential width of the bundles can each be greater than about 0.07 inches or less than about 0.04 inches. The circumferential width of each of the bundles 260, 270, 280, 290 can vary depending on the thickness of the wires 220, the thickness of the cords 230, or a jacket or shield thickness.

The bundles 260, 270, 280, 290 can each have a central axis. The first bundle 260 can have a first central axis, while the second bundle 270 a second central axis, the third bundle 280 a third central axis, and the fourth bundle 290 a fourth central axis. The central axes of the bundles 260, 270, 280, 290 can be different. For example, the first central axis of the first bundle 260 is different from the second, third, and fourth central axis of the bundles 270, 280, 290. The bundles 260, 270, 280, 290 can be placed within the cable 200 such that they are not concentric.

Some of the bundles of the cable 200 can be grouped together. For example, the first bundle 260 and the second bundle 270 can be grouped together and encased within an insulator or a separator. Similarly, the third bundle 280 and the fourth bundle 290 can be grouped together and encased with another insulator or another separator.

The bundles 260, 270, 280, 290 can carry different signals. For example, the wires 220 of the first bundle 260 can transmit signals between the detectors 126 of the noninvasive optical sensor 104 and the front end 116. The wires 220 of the second bundle 270 and the fourth bundle 290 can transmit signals between the emitter drivers 114 and the emitters 122 of the noninvasive optical sensor 104. The emitters 122 can be a light emitting diode (LED) that has a cathode side and an anode side, where a voltage difference between the cathode side and the anode side can facilitate generation of light. The wires 220 of the second bundle 270 can transmit signals between the cathode sides of the emitters 122 and the emitter driving circuit 114, while the wires 220 of the fourth bundle 290 can transmit signal between the anode sides of the emitters 122 and the emitter driving circuit 114. The wires 220 of the third bundle 280 can transmit signals between the memory device 132 of the noninvasive optical sensor 104 and the microprocessor 118 of the patient monitor 102.

The insulators 224 of the wires 220 can have different colors. The different colors can denote different signals the wires 220 carry. For example, one the insulators 224 that are green can denote one of the wires 220 that carries an input signal for the emitters 122, one of the insulators 224 that is white can denote one of the wires 220 that carries an output signal from the detector 126, one of the insulators 224 that is black may indicate that one of the wires 220 that does not carry any signal, and one of the insulators 224 that is purple or pink may indicate one of the wires 220 that carries a signal related to a thermometer. The wires 220 having the insulators 224 in different colors can further assist in a manufacturing process for the cable 200.

The bundles 260, 270, 280, 290 can allow one-way or two-way signal transmission between the noninvasive optical sensor 104 and the patient monitor 102. For example, a first of the wires 220 of the first bundle 260 can transmit signal to the detectors 126 while a second of the wires 220 of the first bundle 260 can receive signal from the detectors 126. In another example, the wires 220 of the second bundle 270 and the fourth bundle 290 can each communicate signals between the cathode/anode sides of the emitters 122 and the emitter driving circuit 114. The wires 220 of the third bundle 280 can each communicate signals between the memory device 132 and the microprocessor 118.

The cable 200 can include additional bundles for transmitting additional patient sensor data or parameters between the noninvasive optical sensor 104 and the patient monitor 102. For example, the noninvasive optical sensor 104 can include the temperature sensor 130, and the cable 200 can include a bundle with one or more of the wires 220 or the cords 230 to transmit signals between the temperature sensor 130 and the microprocessor 118.

The cords 230 can have a coextruded PVC sheath for reducing triboelectric noise generated by frictional contact between different cable elements. The cords 230 may not carry electronic signals. The cords 230 may drain triboelectric induced charges away from the insulator 224 as well as or better than the graphite coating and PVC sheath. As with the PVC sheath, grouping of the cords 230 with the wires 220 can increase the eventual signal quality output from signal processing circuitry, such as, for example, a differential amplifier. For example, use of the cords 230 in a manner that maintains the close physical proximity of the wires 220 tends to ensure external noise applied to the cable 200 is applied substantially equally (or common) to each of the wires 220. Thus, a differential amplifier (not shown) of the patient monitor 102 can effectively filter the applied external noise through, for example, the amplifier's common mode rejection.

Thus, while potentially exhibiting the same or superior advantageous characteristics of the coating or sheath, the cords 230 can be easier to control, cause less rigidity (for example, result in a more flexible bundle), and provide more straightforward processes during manufacturing than the coating or sheath. For example, the cords 230 may be simply cut away at points of connectivity for the wires 220 to circuit substrates or other electrical components. Moreover, the bundles 260, 270, 280, 290 can be made with the cords 230 that are hallow or thinner than the foregoing coatings or sheath. For these and other reasons, the cords 230 may provide for less expensive manufacturing processes.

The first bundle 260 can include an inner shield 226 and an inner jacket 228. The inner shield 226 and the inner jacket 228 can at least partially surround the wires 220 or the cords 230 of the first bundle 260. The inner shield 226 can advantageously reduce electromagnetic interference (EMI) between each of and crosstalk between the wires 220 or the cords 230. The inner shield 226 can be circumferentially surrounded by the inner jacket 228. One or more or all of the bundles 260, 270, 280, 290 can include the inner shield 226 and the inner jacket 228.

The inner shield 226 can be constructed of conductive materials or other suitable shield materials to meet performance or design objectives. Copper, silver, or other suitable materials can be used as materials for the inner shield 226. For example, the inner shield 226 can be constructed using braided copper strands. In another example, the inner shield 226 can be constructed using spiral copper strands. The thickness of the inner shield 226 can also be set to meet design objectives. The inner shield 226 can range in size from 44 AWG to 40 AWG. For example, the inner shield 226 is 44 AWG, tinned copper, with a ninety percent minimum coverage.

The inner jacket 228 can be designed to meet certain design or performance objectives. The inner jacket 228 can be constructed out of the jacket materials previously disclosed or other suitable materials. For example, the inner jacket 228 can be constructed from polytetrafluoroethylene, or PFTE, which allows the bundles 260, 270, 280, 290 to move more freely within the outer shield 206 with a decreased amount of friction between cable elements (for example, bundles 260, 270, 280, 290, the core 210, and the outer shield 206). In this regard, the inner jacket 228 can increase the flexibility of the cable 200 during twisting or kinking motions and prevent kinks from developing within the cable 200 after repeated use.

The inner jacket 228 can be constructed by layering materials. The inner jacket 228 can be constructed with a single sintered PFTE wrap plus a single unsintered PFTE wrap or be PVC with a single PFTE wrap. The inner jacket 228 can range in size from 0.001 inches to 0.1 inches. For example, the inner jacket 228 ranges in size from 0.002 inches to 0.008 inches. In one implementation, the inner jacket 228 is a sintered PFTE film that is approximately 0.0012 inches thick and a single layer of unsintered PFTE film that is approximately 0.004 inches thick.

The core 210 can be positioned between the bundles 260, 270, 280, 290 as shown in FIG. 2A-2C. The bundles 260, 270, 280, 290 can wrapped, twisted, or braided around the core 210 such that the core 210 defines a central axis of the cable 200. The number of the bundles surrounding or wrapping the core 210 can vary depending upon desired cable thickness, shape, size such as outer diameter, rigidity or flexibility, conductive performance, cost, and the like. The bundles 260, 270, 280, 290 can be weaved around the core 210. The core 210 and any one of the bundles 260, 270, 280, 290 may or may not share the same axis with another of the bundles 260, 270, 280, 290. The core 210 and any one of the bundles 260, 270, 280, 290 may or may not be concentric with respect to one another.

It can be advantageous to have the core 210 define a central axis of the cable 200. When the core 210 defines the central axis of the cable 200, more of the tensile stress on the cable 200 can be placed on the core 210 than the wires 220 or cords 230. Therefore, having the core 210 at a center of the cable 200 can reduce the tensile stress on individual components of the cable 200, including each of the bundles 260, 270, 280, 290, and increase the durability of the cable 200. Having the core 210 can evenly distribute stresses on the bundles 260, 270, 280, 290, the wires 220, and the cords 230 away from the central axis of the cable 200 during a kinking motion. The stress on the bundles 260, 270, 280, 290 can be torsional, shear, or tensional stress.

The cross-section of the core 210 can vary. For example, the core 210 can have a cross-section that is substantially rectangular, circular, elliptical, or another shape. The cross-sectional dimension or area of the core 210 can vary along the length of the core 210. The dimensions of the core 210 can be substantially the same as the circumferential width of the bundles within the cable 200. The width of the core 210 can be less than or greater than the circumferential width of one of the bundles 260, 270. 280, 290.

The dimensions of the core 210 can affect the interactions between the bundles 260, 270, 280, 290. For example, if the core 210 has a width less than the circumferential width of one or more of the bundles 260, 270, 280, 290, the core 210 may not prevent the bundles 260, 270, 280, 290 from contacting each other. If the core 210 has a width greater than the circumferential width of one or more the bundles 260, 270, 280, 290, the core 210 may reduce the amount of or prevent the contact between the bundles 260, 270, 280, 290. The reduction in or prevention of the contact between the bundles 260, 270, 280, 290 can reduce the amount of stress or friction generated between the bundles 260, 270, 280, 290.

In some examples, a ratio of the width of the core 210 to the circumferential width of one of the bundles 260, 270, 280, 290 may affect the interactions between the bundles 260, 270, 280, 290. The ratio of the width of the core 210 to the circumferential width of one of the bundles 260, 270, 280, 290 can be between about 0.3 and about 0.7, between about 0.35 and about 0.65, between about 0.4 and about 0.6, between about 0.45 and about 0.55, between about 0.48 and about 0.52, or about 0.3, about 0.35, about 0.4, about 0.45, about 0.5, about 0.55, about 0.6, about 0.65, about 0.7, or ranges between any two of aforementioned values. The ratio of the width of the core 210 to the circumferential width of one of the bundles 260, 270, 280, 290 can be greater than about 0.7 or less than about 0.3. The ratio of the width of the core 210 to the circumferential width of one of the bundles 260, 270, 280, 290 can vary depending on the size of one or more of the bundles 260, 270, 280, 290, the size of the core 210, the desired flexibility or rigidity of the cable 200, the number of bundles in the cable 200, or the like.

The core 210 can include arcuate surfaces 212 (which can be concave) that interact with outer surfaces of the inner jacket 228. The arcuate surfaces 212 of the core 210 can increase the durability of the inner jackets 228 of the bundles 260, 270, 280, 290 and reduce the overall dimension of the cable 200. The interaction between the core 210 and the inner jackets 228 of the bundles 260, 270, 280, 290 (for instance, pressure from the bundles 260, 270, 280, 290 on the core 210) can cause the arcuate surfaces 212 to form on an outer surface of the core 210. The arcuate surfaces 212 of the core 210 can be formed at least from interaction between the core 210 and the bundles surrounding the core 210. The arcuate surfaces 212 may each have cross-sectional shapes that correspond to outer surfaces of one of the bundles 260, 270, 280, 290. The shapes of the arcuate surfaces 212 may be rigid or may change responsive to the interaction between the core 210 and one or more of the bundles 260, 270, 280, 290. The arcuate surfaces 212 can, as discussed herein, reduce the amount of contact between the bundles 260, 270, 280, 290 and thereby reduce the amount of friction or stress on the bundles 260, 270, 280, 290. This can increase durability of the bundles 260, 270, 280, 290 and the cable 200.

The core 210 can be composed of two or more threads wrapped or weaved around a single thread. For example, the core 210 is composed of three or more threads wrapped or weaved around a single thread.

A cross-sectional area of the core 210 of the cable 200 can vary depending on the dimensions of the bundles 260, 270, 280, 290, number of bundles in the cable 200, diameter of the cable 200, desired rigidity or flexibility, desired durability, cost of manufacturing, conductive performance, or the like. The core 210 can have smaller or larger cross-sectional area than the bundles.

The cable 200 can include more than one core 210. For example, the cable 200 having the bundles 260, 270, 280, 290, as shown in FIG. 2B, can include the core 210 in the middle and four additional cores located in spaces formed between two of the four bundles 260, 270, 280, 290 and the outer shield 206. Those four additional cores can reduce the amount of friction between the bundles 260, 270, 280, 290 or between the bundles 260, 270, 280, 290 and the outer shield 206, thus increasing durability of the bundles 260, 270, 280, 290 and the outer shield 206. The additional cores can have cross-sectional areas or dimensions that vary from or match that of the core 210. For example, the cross-sectional areas of the additional cores may be larger than, smaller than, or the same as that of the core 210.

The core 210 can be made out of materials with high flexibility and tensile strength. For example, the core 210 is made out Kevlar fibers. Placing the core 210 with high flexibility and tensile strength can be advantageous in providing an overall cable construction that is both durable and flexible. The durability and flexibility resulting from having the core 210 in the middle wrapped by bundles 260, 270, 280, 290 can be advantageous in emergency medical situations, where medical assessments and interventions are often made in challenging conditions for electrical cables, such as cable 144 in FIG. 1.

Placing the separator 204 between the outer shield 206 and the outer jacket 202 can be advantageous because it can allow the entire construction (for example, the bundles 260, 270, 280, 290, the core 210, and the outer shield 206) to be more flexible or move freely inside the outer jacket 202 itself. In addition, this configuration can prevent extruded plastic from the outer jacket 202 from penetrating the braids of the outer shield 206. The separator 204 can be made out of materials with high flexibility, chemical resistance, thermal resistance, or electrical resistance. For example, the separator 204 can be made out of polytetrafluoroethylene (PTFE).

The outer shield 206, like the inner shield 226, can reduce EMI between the bundles 260, 270, 280, 290 and with other cables. The outer shield 206 can be composed of braided, tinned copper stranding or braided tinsel-wire stranding, where tinsel-wire is produced by wrapping server strands of thin metal foil around a flexible nylon or textile core. Because the thickness of the foil may be relatively thin, a bend radius imposed on the thin metal foil can be much greater than the thickness of the foil. In this regard, tinsel-wire can have a low probability of metal fatigue and, if used, can provide high tensile strength without impairing flexibility.

The outer jacket 202 can be made out of one or more materials having high flexibility, chemical resistance, high tensile strength, high cut resistance, or elongation properties. Such properties can provide greater protection from kinking and bending due to material properties. For example, the outer jacket 202 can be made out of thermoplastic polyurethane. The outer jacket 202 can have a thickness ranging between about 0.018" and about 0.040", between about 0.02" and about 0.038", between about 0.022" and about 0.036", between about 0.024" and about 0.034", between about 0.026" and about 0.032", between about 0.028" and about 0.030", or about 0.018", about 0.020", about 0.022", about 0.024", about 0.026", about 0.028", about 0.030", about 0.032", about 0.034", about 0.035", about 0.036", about 0.038", about 0.040", or ranges between any two of aforementioned values. The thickness of the outer jacket 202 can be less than 0.018" or greater than about 0.040".

The cable 200 can have an outer diameter ranging between about 0.1" and about 0.4", between about 0.125" and about 0.375", between about 0.15" and about 0.35", between about 0.175" and about 0.325", between about 0.2" and about 0.3", between about 0.225" and about 0.275", or about 0.1", about 0.125", about 0.15", about 0.175", about 0.2", about 0.225", about 0.235", about 0.25", about 0.275", about 0.3", about 0.325", about 0.35", about 0.375", about 0.4", or ranges between any two of aforementioned values. The outer diameter of the cable 200 can be less than 0.125" or greater than about 0.40".

Terminology

The following description is merely illustrative in nature and is in no way intended to limit the disclosure, its application, or uses. For purposes of clarity, the same reference numbers will be used in the drawings to identify similar elements. It should be understood that steps within a method may be executed in different order without altering the principles of the present disclosure.

Conditional language used herein, such as, among others, "can," "might," "may," "for example," and the like, unless specifically stated otherwise, or otherwise understood within the context as used, is generally intended to convey that certain embodiments include, while other embodiments do not include, certain features, elements or states. Thus, such conditional language is not generally intended to imply that features, elements or states are in any way required for one or more embodiments or that one or more embodiments necessarily include logic for deciding, with or without author input or prompting, whether these features, elements or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Terms such as "substantially," "about," "approximately" or the like as used in referring to a relationship between two objects is intended to reflect not only an exact relationship but also variances in that relationship that may be due to various factors such as the effects of environmental conditions, common error tolerances, manufacturing variances, or the like. It should further be understood that although some values or other relationships may be expressed herein without a modifier, these values or other relationships may also be exact or may include a degree of variation due to various factors such as the effects of environmental conditions, common error tolerances, or the like. For example, when referring to measurements, about a specified measurement can, in some contexts, refer to a measurement variation of around equal to or less than ±10%, ±5%, ±2%, or ±1% (such as a variation of ±10%, ±5%, ±2%, ±1%, ±0.8%, ±0.5%, or ±0.3%) from the specified measurement.

Although the low noise oximetry cable including cords is disclosed with reference to few various examples, the disclosure is not intended to be limited thereby. For example, the cords may not be hollow, may include a conductor or other conductive materials, may include only conductors of any suitably flexible material. Moreover, use of blank hollow cords may advantageously apply flexibility in a wide variety of applications, including cabling for virtually any medically monitored signals such as those invasively or noninvasively acquired signals relating to heart or brain activity or condition, spinal activity or condition, circulation parameters, tissue health, or the like. Moreover, the cabling may include only one or more portions of the communication link between sensor components and monitor electronics. The cable may also be an integral part of a reusable, disposable or combination sensor. Moreover, the addition of cords for shielding sensitive cabling may advantageously be applied generally to any and all cabling environments, and particularly in environments susceptible to triboelectric noise.

Additionally, other combinations, omissions, substitutions and modifications will be apparent to the skilled artisan in view of the disclosure herein. Accordingly, the present disclosure is not intended to be limited by the examples, but is to be defined by reference to the appended claims.

Additionally, all publications, patents, and patent applications mentioned in this specification are herein incorporated by reference to the same extent as if each individual publication, patent, or patent application was specifically and individually indicated to be incorporated by reference.

What is claimed is:

1. An oximetry system capable of acquiring signals indicative of one or more physiological parameters of a patient, the oximetry system comprising:
    a noninvasive sensor comprising a detector configured to detect light attenuated by a body tissue of a patient and output a detector signal indicative of the light detected after attenuation by the body tissue;
    a patient monitor configured to receive the detector signal and determine one or more physiological parameters for the patient from the detector signal; and
    a cable comprising:
        a core comprising a plurality of fibers;
        a plurality of bundles comprising a first bundle and a second bundle, the first bundle comprising a first plurality of wires and an inner shield at least partially surrounding the first plurality of wires, the second bundle comprising a second plurality of wires, the inner shield being configured to provide electromagnetic interference protection;
        an outer shield at least partially surrounding the first bundle and the second bundle and configured to provide electromagnetic interference protection; and
        a jacket at least partially surrounding the outer shield, wherein no bundle of the plurality of bundles is concentric with the core.

2. The oximetry system of claim 1, wherein the noninvasive sensor comprises a sensor housing configured to position an emitter and the detector proximate to the body tissue, and the one or more physiological parameters comprise an oxygen saturation and a pulse rate, the first bundle being configured to transmit the detector signal from the noninvasive sensor to the patient monitor.

3. The oximetry system of claim 1, wherein the core is flexible and configured to reduce a tensile stress exerted on the cable and increase a durability of the cable.

4. The oximetry system of claim 3, wherein the first bundle and the second bundle are twisted or weaved around the core.

5. The oximetry system of claim 1, wherein the inner shield comprises a metal.

6. The oximetry system of claim 1, wherein the cable comprises a third bundle at least partially surrounded by the outer shield, the third bundle comprising a third plurality of wires.

7. The oximetry system of claim 6, wherein the first bundle, the second bundle, and the third bundle are twisted or weaved around the core.

8. The oximetry system of claim 1, wherein the first bundle and the second bundle are not concentric with each other.

9. The oximetry system of claim 5, wherein the metal comprises a copper or a silver.

10. The oximetry system of claim 1, wherein the first bundle comprises a different number of wires than the second bundle.

11. The oximetry system of claim 1, wherein the core comprises a plurality, of arcuate surfaces that contact the first bundle and the second bundle and limit an amount of contact between the first bundle and the second bundle.

12. The oximetry system of claim 11, wherein the plurality of arcuate surfaces are formed at least partly by pressure from the first bundle and the second bundle on the core.

13. A cable for transmitting signals in an oximetry system, the cable comprising:
    a plurality of bundles comprising a first bundle and a second bundle, the first bundle comprising a first plurality of wires and an inner shield at least partially surrounding the first plurality of wires, the second bundle comprising a second plurality of wires, the inner shield being configured to provide electromagnetic interference protection;
    a core comprising a plurality of fibers and configured to reduce a tensile stress exerted on the cable and increase a durability of the cable; and
    an outer shield at least partially surrounding the first bundle and the second bundle and configured to provide electromagnetic interference protection,
    wherein no bundle of the plurality of bundles is concentric with the core.

14. The cable of claim 13, wherein the first bundle and the second bundle are twisted or weaved around the core.

15. The cable of claim 13, wherein the second bundle comprises a second shield at least partially surrounding the second plurality of wires, the second shield being configured to provide electromagnetic interference protection.

16. The cable of claim 13, further comprising a third bundle disposed within a jacket along with the first bundle and the second bundle.

17. The cable of claim 13, wherein the first bundle and the second bundle are not concentric with each other.

18. The cable of claim 13, wherein the core defines a central axis for the cable.

19. The cable of claim 13, wherein the first bundle comprises a different number of wires than the second bundle.

20. A method of manufacturing a cable for transmitting signals in an oximetry system, the method comprising:
    assembling a first bundle comprising a first plurality of wires and an inner shield at least partially surrounding the first plurality of wires, the inner shield being configured to provide electromagnetic interference protection;
    assembling a second bundle comprising a second plurality of wires; and
    placing, within a jacket and an outer shield, the first bundle and the second bundle adjacent to a core so that the first bundle and the second bundle are not concentric with the core, the outer shield being configured to provide electromagnetic interference protection, the core comprising a plurality of fibers.

21. The method of claim 20, further comprising twisting or weaving the first bundle and the second bundle around the core.

22. The method of claim 20, wherein said placing comprises placing, within the jacket and the outer shield, a third bundle adjacent to the core, the third bundle comprising a third plurality of wires.

23. The method of claim 22, further comprising twisting or weaving the first bundle, the second bundle, and the third bundle around the core.

24. The method of claim 20, wherein said placing comprises placing the first bundle and the second bundle so that the first bundle and the second bundle are not concentric with each other.

25. The method of claim 20, wherein said placing comprises placing the first bundle and the second bundle adjacent to the core so that the core defines a central axis for the cable.

\* \* \* \* \*